(12) United States Patent
Kumar et al.

(10) Patent No.: US 9,044,427 B2
(45) Date of Patent: Jun. 2, 2015

(54) COMPOSITIONS AND METHODS FOR PREVENTION AND TREATMENT OF WOUNDS

(75) Inventors: Ramesh Kumar, Pennington, NJ (US); Manoj Maniar, Fremont, CA (US)

(73) Assignee: ONCONOVA THERAPEUTICS, INC, Newtown, NJ (US)

( * ) Notice: Subject to any disclaimer, the term of this patent is extended or adjusted under 35 U.S.C. 154(b) by 0 days.

(21) Appl. No.: 13/636,305

(22) PCT Filed: Mar. 24, 2011

(86) PCT No.: PCT/US2011/029817
§ 371 (c)(1),
(2), (4) Date: Sep. 20, 2012

(87) PCT Pub. No.: WO2011/119848
PCT Pub. Date: Sep. 29, 2011

(65) Prior Publication Data
US 2013/0012588 A1    Jan. 10, 2013

Related U.S. Application Data

(60) Provisional application No. 61/316,932, filed on Mar. 24, 2010.

(51) Int. Cl.
*A61K 31/10* (2006.01)
*A61K 9/08* (2006.01)
*A61P 17/02* (2006.01)
*A61K 9/00* (2006.01)

(52) U.S. Cl.
CPC .............. *A61K 31/10* (2013.01); *A61K 9/0019* (2013.01)

(58) Field of Classification Search
CPC ............................. A61K 31/10; A61K 9/0019
USPC ....... 514/710, 709, 568; 568/34, 28
See application file for complete search history.

(56) References Cited

U.S. PATENT DOCUMENTS

2011/0250184 A1*  10/2011  Kumar ................. 424/93.7

FOREIGN PATENT DOCUMENTS

WO    WO 2008/105808    *  9/2008  ........... A61K 31/407

OTHER PUBLICATIONS

Pechkovsky et al. J. Biol. Chem. 2008, 283, 12898-12908.*
Dash S K et al.: "Preformulation development of a parenteral formulation for ON 01210.Na, a radioprotectant" AAPS Annual Meeting and Exposition,(Online] Nov. 5, 2005.
Alfieri A A et al: "Radiation damage protection by the benzylstyryl sulfone analog, Ex-Rad" International Journal of Radiation Oncology Biology Physics, vol. 60, No. 1(2004).
Strickley et al: "Solubilizing Exipients in Oral and Injectable Formulations" Pharmaceutical Research, Kluwe Academic Publishers, New York, NY, US vol. 21, No. 2, (2004).

* cited by examiner

*Primary Examiner* — Sreeni Padmanabhan
*Assistant Examiner* — Irina Neagu
(74) *Attorney, Agent, or Firm* — Houri Khalilian; Serge Sira; Law Offices of Khalilian Sira, LLC

(57) ABSTRACT

The present invention provides compositions and methods for promoting rapid healing and/or regeneration of damaged tissue resulting from a wound comprising administering to a subject in need thereof a therapeutically effective amount of a pharmaceutical composition comprising a compound of (E)-4-carboxystyryl-4-chlorobenzylsulfone, or a functional derivative thereof, and a pharmaceutically acceptable excipient.

9 Claims, 1 Drawing Sheet

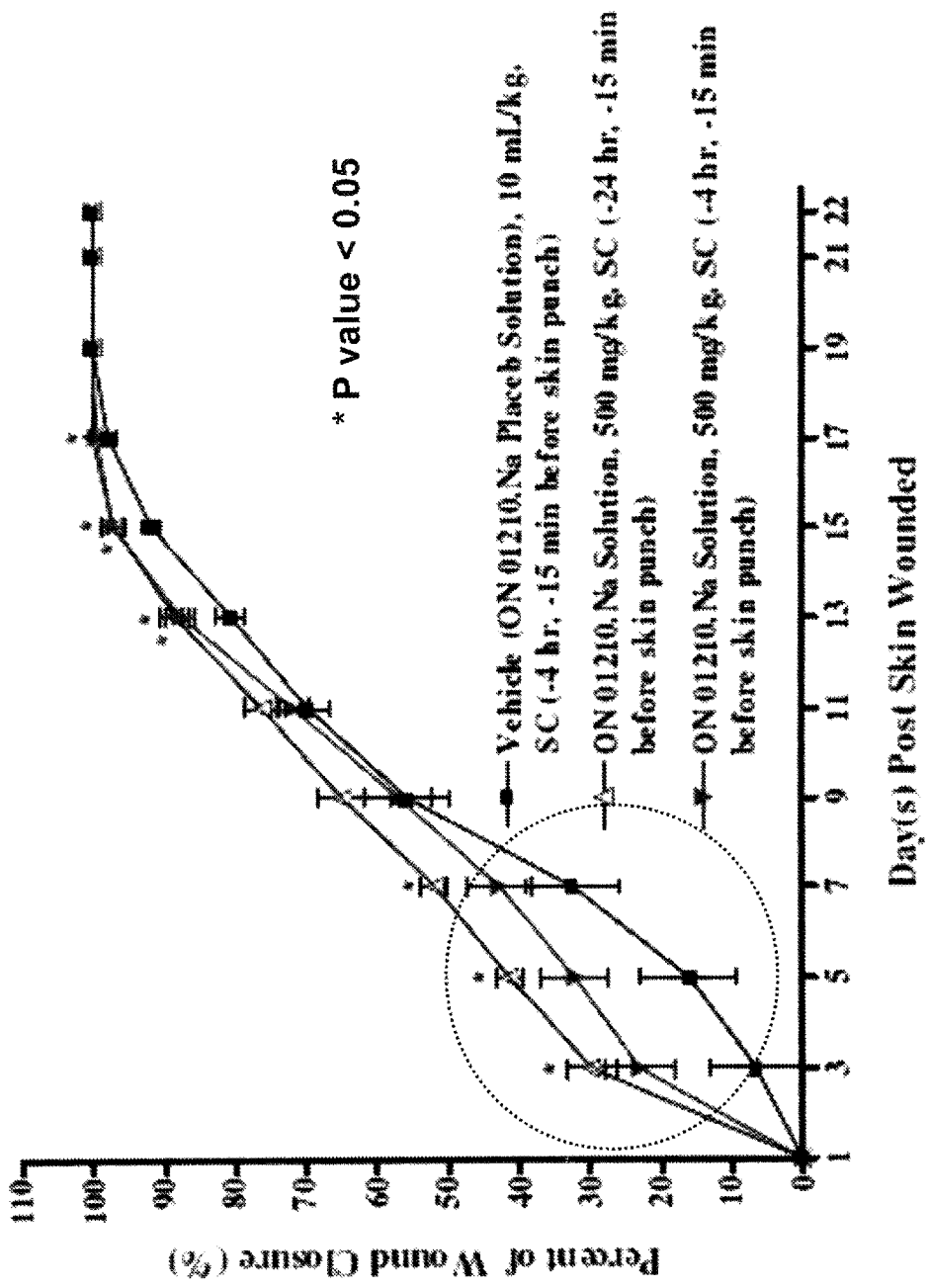

COMPOSITIONS AND METHODS FOR PREVENTION AND TREATMENT OF WOUNDS

This application is a National Stage entry of International Application No. PCT/US2011/029817, filed on 24 Mar., 2011, which claims priority to U.S. Provisional Patent Application No. 61/316,932 filed on 24 Mar., 2010, the entire contents of which are incorporated herein by reference.

FIELD OF THE INVENTION

This invention relates generally to beneficial effects obtained via administration of a pharmaceutical composition for the treatment and/or prevention of skin wounds in warm-blooded animals, such as mammals and especially humans.

BACKGROUND OF THE INVENTION

The compounds of $\alpha,\beta$-unsaturated aryl sulfones are small molecule kinase regulatory compounds that have been developed for modifying cell cycle distribution patterns in cancer cells subjected to radiation therapy, and they have been identified as a potential candidate for radiation protection studies. These compounds are described in U.S. Pat. Nos. 6,656,973 and 6,667,346, which are particularly incorporated herein by reference in their entirety.

Certain compounds of $\alpha,\beta$-unsaturated aryl sulfones and specific formulations regarding suspension and/or aqueous compositions of these compounds have also been previously described in the PCT Application WO 2007/016201 and the PCT Application WO 2008/105808, contents of which are particularly incorporated herein by reference in their entireties The $\alpha,\beta$-unsaturated aryl sulfones, in particular $\alpha,\beta$ unsaturated benzyl styryl sulfones, have demonstrated significant and selective systemic protection of normal cells from radiation-induced damage in animals. It has also been demonstrated that compounds of $\alpha,\beta$-unsaturated aryl sulfones exhibit protection of DNA, bone marrow, stem cells, gastrointestinal crypt cells, and amelioration of cytopenia from radiation. These classes of compounds have also shown to possess antiproliferative activity and selectivity in the killing of proliferating cells such as tumor cells, but not normal cells.

Radiation protection provided by compounds of $\alpha,\beta$-unsaturated aryl sulfone is achieved through regulation levels of pro-apoptosis proteins such as p53 as well as its downstream regulators p21, Bax, c-Abl and p73, indicating that these compounds could rescue cells from ionizing radiation-induced p53-dependent apoptosis. Sanchita P. Ghosh et al, Radiation Protection by a New Chemical Entity, Ex-Rad: Efficacy and Mechanisms, Radiation Research 171,000-000 (2009).

While apoptosis has been previously described for many physiological processes, one area that has only recently been under investigation is skin wound healing. Apoptosis is vital to normal wound healing, especially in the removal of inflammatory cells and scar formation. As cell populations rapidly proliferate during tissue reconstruction, cell growth is balanced by apoptosis. Inflammatory cells, for example, must be removed in order to begin the next stage of wound healing. Otherwise, persistent inflammation can lead to non healing wounds. Similarly, the granulation tissue must decrease in cellularity to evolve into a scar. Recent research has elucidated some of the key roles of apoptosis in the wound healing process.

The role of pro-apoptosis protein P21 in modulation and repair of wounds has previously been demonstrated by Michelle Olive et al. "p21 modulats arterial wound repair" in J Clin Invest.; 118(6): 2050-2061 2008. It has been demonstrated that that p21 is a key mediator of vascular proliferation in response to injury and that p21 modulates arterial wound repair and its activity is essential for the regulation of cell proliferation and inflammation after arterial injury in local vascular cells.

U.S. Pat. No. 6,486,210 discloses compounds of $\alpha,\beta$-unsaturated aryl sulfone having demonstrated apoptosis and anticancer chemotherapeutic activities through binding to target receptor tyrosine kinases such as Mitogen Activated Protein Kinase (MAPK) that result in regulating the kinase cascade (e.g., Ras/Raf/MEK/ERK kinase cascade). The best understood MAPK pathway involves extracellular signal-regulated kinases which constitute the Ras/Raf/MEK/ERK kinase cascade (Boudewijn et al., Trends Biochem. Sci. 20, 18 (1995)). Once this pathway is activated by different stimuli, MAPK phosphorylates a variety of proteins including several transcription factors which translocate into the nucleus and activate gene transcription. Negative regulation of this pathway could arrest the cascade of these events.

It has been shown that MAPK has a critical role in the proliferation and control of hematopoietic progenitor cells. Masayuki Towatari et al. The Journal of Biological Chemistry, 270, 4101-4107 (1995.) It has also been shown that MAPK is involved in activation of osteogenic differentiation of adult stem cells and suggest that commitment of cells into osteogenic or adipogenic lineages is governed by activation or inhibition of family members of mitogen activatedprotein kinase. Rama K. Jaiswal et al, The American Society for Biochemistry and Molecular Biology, Inc. Vol. 275, No. 13, pp. 9645-9652 (2000).

Stem cells including hematopoietic stem cells have very important roles in a number of different processes in the body. For example, leukocytic hematopoietic cells are important in maintaining the body's defenses against disease; monocytes, macrophages and lymphocytes are involved in potentiating the body's responses to infection and tumors, while granulocytes are involved in overcoming infection, parasites and tumors. Platelets, another hematopoietic cell, form an important element in the hemostatic mechanism through initiating thrombus formation by their adhesion to each other and to damaged surfaces, and by the release of factors which assist in the formation of the fibrin clot. Erythrocytes are mainly involved in the transport of oxygen.

Recruitment of stem cells and/or progenitor cells is important in a variety of applications related to inflammation and wound healing. Vasculogenesis, which involves the growth of vessels derived from endothelial progenitor cells, is an example of such a process. Vasculogenesis, as well as angiogenesis, the process by which new blood vessels are formed from extant capillaries, and the factors that regulate these processes, are important in inflammation, and wound healing, and also contribute to pathologic conditions such as tumor growth, diabetic retinopathy, rheumatoid arthritis, and chronic inflammatory diseases (see, e.g., U.S. Pat. No. 5,318, 957; Yancopoulos et al. Cell 93:661-4 (1998); Folkman et al. Cell 87; 1153-5 (1996); and Hanahan et al. Cell 86:353-64 (1996)).

Both angiogenesis and vasculogenesis involve the proliferation of endothelial cells. Endothelial cells line the walls of blood vessels; capillaries are comprised almost entirely of endothelial cells. The angiogenic process involves not only increased endothelial cell proliferation, but also comprises a cascade of additional events, including protease secretion by endothelial cells, degradation of the basement membrane, migration through the surrounding matrix, proliferation, alignment, differentiation into tube-like structures, and synthesis of a new basement membrane. Vasculogenesis involves recruitment and differentiation of mesenchymal cells into angioblasts, which then differentiate into endothelial cells which then form de novo vessels (see, e.g., Folkman et al. Cell 87:1153-5, (1996)).

There is an intense interest in therapeutic protocols that are well-tolerated by the subject, but that are of high potency in effecting stimulation of stem cell and/or progenitor cell recruitment to treat inflammation and affect wound healing. The methods and compositions of the present invention satisfy these and other long felt needs with the following invention.

SUMMARY OF THE INVENTION

The invention disclosed herein provides methods and composition for promoting rapid healing and/or regeneration of damaged tissue resulting from a wound comprising administering to a subject in need thereof a therapeutically effective amount of a pharmaceutical composition comprising a compound of (E)-4-carboxystyryl-4-chlorobenzylsulfone, or a functional derivative thereof, and a pharmaceutically acceptable excipient, wherein said pharmaceutical composition promotes rapid healing and/or regeneration of damaged tissues while retaining original composition of the tissue and minimizing complications and scarring.

In one embodiment, the administration to the subject is performed prior to the incident of the wound, concomitant with formation or incident of the wound, or after formation of the wound, or a combination thereof. In a preferred embodiment, the administration to the subject is performed prior to the incident of the wound.

In another embodiment, the administration to the subject is performed about 4 hours prior to the incident of the wound, and/or about 24 hours prior to the incident of the wound.

In one embodiment, the composition of the invention comprises a compound of (E)-4-carboxystyryl-4-chlorobenzylsulfone, such as for example, ON 01210.Na. In another embodiment, ON 01210.Na is formulated in an aqueous solution composition comprising between about 20 mg/ml to about 100 mg/ml of ON 01210.Na, and a cosolvent comprising a water soluble polymer including, by way of example and not limitation, polyethylene glycol (PEG), polypropylene glycol, polyglycerol, DMA, propylene glycol, glycerol, ethanol, sorbitol, and isopropyl alcohol, or a combination thereof, in an amount between about 25% and about 90% w/v, wherein the composition has a pH within the range of about 7.0 to about 9.5.

The composition is administered through several routes, including by way of example and not limitation, parenteral routes, topical routes, oral routes, or a combination thereof.

In another aspect, the invention provides a method for controlling or alleviating pain by reducing the severity of inflammation associated with a wound or damaged tissues comprising administering to a subject in need thereof a therapeutically effective amount of a pharmaceutical composition comprising a compound of (E)-4-carboxystyryl-4-chlorobenzylsulfone, or a functional derivative thereof; wherein the subject treated with the composition demonstrates an accelerated healing process as compared to control non-treated subjects.

In one embodiment, the healing process is at least four times faster in subjects treated with the composition of the invention versus the control non-treated subjects when measured after 3 days from incident of the wound.

In another aspect, the invention provides a method of relieving or ameliorating symptoms of disorders related to tissue destruction or dysfunction and pain or symptoms associated with wounds in a mammal comprising administering to a subject in need thereof a therapeutically effective amount of a pharmaceutical composition comprising a compound of (E)-4-carboxystyryl-4-chlorobenzylsulfone, or a functional derivative thereof, in combination with one or more anti-inflammatory compounds; and a pharmaceutically acceptable carrier or diluent, wherein said pharmaceutical composition inhibits one or more components of the inflammatory pathway, and wherein severity of said symptoms are reduced in the mammal.

In one embodiment, the wound is an incised wound, a lacerated wound, a penetrating wound, a perforated wound, a puncture wound, an open wound, or a subcutaneous wound, or a combination thereof.

In another embodiment, the wound is a consequence of a disease or disorder, surgery, accident, or a combination thereof.

In yet another embodiment, the wound is external wound, internal wound, or a combination thereof.

Other preferred embodiments of the invention will be apparent to one of ordinary skill in the art in light of what is known in the art, in light of the following drawings and description of the invention, and in light of the claims.

BRIEF DESCRIPTION OF THE DRAWINGS

FIG. 1 Illustrates significant improvement in wound healing in subjects pre-treated with a composition containing ON 01210. Na. Percentage of wound closure has been shown for 3 classes of subjects, namely, subjects pre-treated with ON 01210. Na 24 hour prior to wound, subjects pre-treated with ON 01210. Na 4 hour prior to wound, and subject pre-treated with placebo (negative control.).

DETAILED DESCRIPTION OF THE INVENTION

Definitions:

As used herein, the term "cytokine" is a generic term for proteins released by one cell population which act on another cell as intercellular mediators. Examples of such cytokines are tumor necrosis factor (TNF$\alpha$ or $\beta$); colony stimulating factors (CSFs) such as macrophage-CSF (M-CSF); granulocyte-macrophage-CSF (GM-CSF); and granulocyte-CSF (G-CSF); interleukins (ILs) such as IL-1, IL-2, IL-8, IL-12, or IL-18; and other polypeptide factors including leukemia inhibitory factor (LIF) and kit ligand (KL). As used herein, the term cytokine includes proteins from natural sources or from recombinant cell culture and biologically active equivalents of the native sequence cytokines.

As used herein, "about" referrers to numerical values that are within the range of 10% above or 10% below the stated numerical value.

As used herein, a numerical range includes all its integer amounts. It is intended herein that by recitation of any specified ranges, the ranges recited also include all those specific integer amounts between the recited range. For example, in the range of about 75% and 100%, includes numerical values of 76% to 99%, 77% to 98%, etc, without actually reciting each specific range therewith.

As used herein, "therapy" is generically used to include all clinical applications including diagnostic, prevention, treatment and amelioration of symptoms of a wound and diseases and disorders associated with the wound.

As used herein, "α,β unsaturated aryl sulfone" is meant a chemical compound containing one or more α,β unsaturated aryl sulfone groups, wherein aryl can be substituted or unsubstituted and the hydrogen atoms attached to the α and β carbons are optionally replaced by other chemical groups.

As used herein, "substituted" means that an atom or group of atoms has replaced hydrogen as the substituent attached to a ring atom. The degree of substitution in a ring system may be mono-, di-, tri- or higher substitution.

As used herein, "aryl" employed alone or in combination with other terms, means, unless otherwise stated, a carbocyclic aromatic system containing one or more rings (typically one, two or three rings) wherein such rings may be attached together in a pendent manner or may be fused. Examples include phenyl; anthracyl; and naphthyl, particularly, 1-naphthyl and 2-naphthyl. The aforementioned listing of aryl moieties is intended to be representative, not limiting. It is understood that the term "aryl" is not limited to ring systems with six members.

As used herein, "heteroaryl" by itself or as part of another substituent means, unless otherwise stated, an unsubstituted or substituted, stable, mono- or multicyclic heterocyclic aromatic ring system which consists of carbon atoms and from one to four heteroatoms selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom which affords a stable structure.

Examples of such heteroaryls include benzimidazolyl, particularly 2-benzimidazolyl; benzofuryl, particularly 3-, 4-, 5-, 6- and 7-benzofuryl; 2-benzothiazolyl and 5-benzothiazolyl; benzothienyl, particularly 3-, 4-, 5-, 6-, and 7-benzothienyl; 4-(2-benzyloxazolyl); furyl, particularly 2- and 3-furyl; isoquinolyl, particularly 1- and 5-isoquinolyl; isoxazolyl, particularly 3-, 4- and 5-isoxazolyl; imidazolyl, particularly 2-, -4 and 5-imidazolyl; indolyl, particularly 3-, 4-, 5-, 6- and 7-indolyl; oxazolyl, particularly 2-, 4- and 5-oxazolyl; purinyl; pyrrolyl, particularly 2-pyrrolyl, 3-pyrrolyl; pyrazolyl, particularly 3- and 5-pyrazolyl; pyrazinyl, particularly 2-pyrazinyl; pyridazinyl, particularly 3- and 4-pyridazinyl; pyridyl, particularly 2-, 3- and 4-pyridyl; pyrimidinyl, particularly 2- and 4-pyrimidinyl; quinoxalinyl, particularly 2- and 5-quinoxalinyl; quinolinyl, particularly 2- and 3-quinolinyl; 5-tetrazolyl; 2-thiazolyl; particularly 2-thiazolyl, 4-thiazolyl and 5-thiazolyl; thienyl, particularly 2- and 3-thienyl; and 3-(1,2,4-triazolyl). The aforementioned listing of heteroaryl moieties is intended to be representative, not limiting.

As used herein, "styryl sulfone" or "styryl sulfone compound" or "styryl sulfone therapeutic" referrers to chemical compounds containing one or more such styryl sulfone groups.

As used herein, "dimethylamino(C2-C6 alkoxy)" refers to (CH3)2N(CH2)nO— wherein n is from 2 to 6. Preferably, n is 2 or 3. Most preferably, n is 2, that is, the group is the dimethylaminoethoxy group, that is, (CH3)2NCH2CH2O—.

As used herein, "phosphonato" refers to the group —PO(OH)2.

As used herein, "sulfamyl" refers to the group —SO2NH2.

As used herein, "halo" or "halogen" includes fluorine, chlorine, bromine and iodine.

As used herein, "phosphate" and "phosphonate" and "phosphonato" refer to the moieties having the following structures:

As used herein "aryl", "aromatic group", or "aromatic ring" contemplates substituted or unsubstituted single-ring aromatic groups (for example, phenyl, pyridyl, pyrazolyl, etc.) and polycyclic ring systems (naphthyl, quinolinyl, etc.). The polycyclic rings may have two or more rings in which two atoms are common to two adjoining rings (the rings are "fused") wherein at least one of the rings is aromatic, e.g., the other rings can be cycloalkyls, cycloalkenyls, aryl, heterocyclic and/or heteroaryls. The aryl group may be optionally substituted with one or more substituents selected from halo, alkyl, CN, NO2, CO2R, C(O)R, —O—R, —N(R')(R"), —N(R)C(O)R, —N(R)SO2R, —SR, —C(O)N(R')(R"), —OC(O)R, —OC(O)N(R')(R"), SO2, —SOR, —SO3R, —SO2N(R')(R"), phosphate, phosphonate, substituted and unsubstituted alkyl, substituted and unsubstituted alkenyl, substituted and unsubstituted cycloalkyl, substituted and unsubstituted cycloalkenyl, substituted and unsubstituted aryl and a substituted and unsubstituted heterocyclic group, wherein the substituted alkyl, substituted alkenyl, substituted cycloalkyl, substituted cycloalkenyl, substituted aryl and substituted heterocyclic group may be substituted with one or more of halo, CN, CF3, CO2R, C(O)R, C(O)NR2, NR2, NO2, and OR.

With respect to the above definitions, each R is independently selected from H, substituted and unsubstituted alkyl, substituted and unsubstituted cycloalkyl, substituted and unsubstituted cycloalkenyl, substituted and unsubstituted alkenyl, substituted and unsubstituted alkynyl, substituted and unsubstituted aralkyl, substituted and unsubstituted aryl and a substituted and unsubstituted heterocyclic group. Each R' and R" are independently selected from H, substituted and unsubstituted alkyl, substituted and unsubstituted cycloalkyl, substituted and unsubstituted cycloalkenyl, substituted and unsubstituted alkenyl, substituted and unsubstituted alkynyl, substituted and unsubstituted aralkyl, substituted and unsubstituted aryl and substituted and unsubstituted heterocyclic group; or R' and R" may be taken together with the nitrogen to which they are attached to form a 5- to 7-membered ring which may optionally contain a further heteroatom. The substituted alkyl, substituted cycloalkyl, substituted cycloalkenyl, substituted alkenyl, substituted alkynyl, substituted aralkyl, substituted aryl and substituted heterocyclic group may be substituted with one or more of halo, CN, CF3, OH, CO2H, NO2, C1-6alkyl, —O—(C1-6alkyl), —NH2, —NH (C1-6alkyl) and —N(C1-6alkyl)2.

As used herein "heteroatom", particularly as a ring heteroatom, refers to N, O, and S.

In the present context the term "wound" denotes a bodily injury with disruption of the normal integrity of tissue structures. The term is also intended to encompass the terms "sore", "lesion", "necrosis" and "ulcer". Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions.

There is often a certain overlap between the use of the terms "wound" and "ulcer" and "wound" and "sore" and, furthermore, the terms are often used at random. Therefore as mentioned above, in the present context the term "wound" encompasses the term "ulcer", "lesion", "sore" and "infarction", and the terms are indiscriminately used unless otherwise indicated.

The term "wound" used in the present context also denotes any wound (see below for a classification of wounds) and at any particular stage in the healing process including the stage before any healing has initiated.

The present invention is concerned with prevention/and or treatment of wound and inflammation-associated tissue damage. The invention is particularly directed to therapeutic methods for treating localized and systemic inflammation associated with wounds as well as the treatment of a variety of diseases that are associated with the wound and/or ensue from a wound.

In a general embodiment, the present invention relates to a method for promoting rapid healing and/or regeneration of damaged tissues resulting from a wound comprising administering to a subject in need thereof a therapeutically effective amount of a pharmaceutical composition comprising an $\alpha,\beta$ unsaturated benzyl styryl sulfone or a functional derivative thereof; and a pharmaceutically acceptable excipient.

Without being bound to any particular mechanism of action, one possible mechanism for the composition of the invention is mobilizing, enhance the trafficking of, and/or recruiting stem cells and/or progenitor cells to the site of the wound or injury.

Also, without being bound to any specific mechanism of action, one other possible mechanism of action for the compositing of the invention is through regulation (suppression and/or stimulation) of expression and synthesis of inflammatory molecules comprising cytokines (for example, IL-1, IL-2, IL-6, IL-8, IL-12, IL-18, TNF$\alpha$ or $\beta$), nitric oxide, reactive oxygen intermediates (ROI), leukotrenes, and/or prostaglandins, or any one or more of the known biological molecules involved in inflammatory signal transduction pathways, etc.

Since an anti-cytokine or anti-inflammatory agents such as $\alpha,\beta$ unsaturated benzyl styryl sulfones and functional derivatives thereof can mobilize, enhance the trafficking of, and/or recruit stem cells and/or progenitor cells to the site of injury, these compounds have the ability to inhibit the edema and inflammatory response and thereby treat or prevent diseases where inflammation contributes to the disease process.

Accordingly, in one embodiment the invention provides a method for promoting rapid healing and/or regeneration of damaged tissue resulting from a wound comprising administering to a subject in need thereof a therapeutically effective amount of a pharmaceutical composition comprising a compound of $\alpha,\beta$ unsaturated benzyl styryl sulfones, or a functional derivative thereof, and a pharmaceutically acceptable excipient, wherein said pharmaceutical composition suppresses the synthesis of cytokines, or any one or more of the known biological molecules involved in the activation of inflammatory signal transduction pathways leading to a blockade of inflammation or reduced immune response, or a combination thereof.

The wounds that are treated using the methods and compositions of the present invention may be acute and/or chronic wounds. Acute wounds are those wounds that heal promptly, within 30 days (or 60 days in diabetics). Chronic wounds include, but are not limited to, pressure sores, surgical wounds, spinal injury wounds, burns, chemical-induced wounds and wounds due to blood vessel disorders. Examples of wounds which can be prevented and/or treated in accordance with the present invention are, e.g., aseptic wounds, contused wounds, incised wounds, abrasions, avulsions, crush wounds, cuts, projectile wounds, puncture wounds, lacerated wounds, non-penetrating wounds (i.e. wounds in which there is no disruption of the skin but there is injury to underlying structures), open wounds, penetrating wound, perforating wounds, septic wounds, subcutaneous wounds, etc. Examples of sores are bed sores, canker sores, diabetic skin sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis), among others.

The kinds of wounds to be treated according to the invention include, by way of example and not limitation, i) general wounds such as, e.g., surgical, traumatic, spinal injury wounds, and wounds due to blood vessel disorders, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

Wound Healing and Scar Formation

Wounds can occur from many sources as is evident from the list supra. An incision created by a surgeon, trauma as a result of blunt force, or tissue death caused by a variety of diseases are some examples but all wounds regardless of their nature undergo a similar process of wound healing. Wound healing occurs in three distinct phases. The first phase is the inflammatory phase that is characterized by inflammation at the site of the trauma. This phase is critical for healing and involves extensive cell migration. The second phase of wound healing is the proliferative phase, which is marked by epithelialization, angiogenesis, granulated tissue formation and collagen deposition. Angiogenesis, which involves new capillary formation, is used to deliver nutrients and maintain granulation. Without formation of new capillaries into the wound, required nutrients fail to reach the wound resulting in a chronically unhealed wound. The final stage of wound healing is the maturational phase wherein fibroblasts differentiate into collagen. The disposition of the connective tissue matrix and collagen undergoes a contraction, thereby resulting in scar tissue. Although scar formation is itself critical to wound healing, unfortunately excessive scar formation can have additional cosmetic and/or pathologic consequences. The composition of this invention is effective in one or more distinct phases of the wound.

In one embodiment, the compositions and methods of the present invention trigger the proper healing sequence required in all forms of wounds and therefore prevent the destructive biochemical reactions typically brought on by a wound.

Scar formation occurs in all tissues and the adverse effects of scar formation include for example, but are not limited to, keloid, hypertrophic scars, burn contracture and scleroderma in skin; stricture, adhesions and chronic pancreatitis in the gastrointestinal tract; cirrhosis and biliary atresia in the liver; interstitial fibrosis and bronchopulmonary dysplasia in the lung; rheumatic disease and ventricular aneurysm in the heart; retrolental fibroplasia and diabetic retinopathy in the eye; transmission loss in nerves; ankylosis and osteoarthritis in the bones and glomerulonephritis in the kidney, etc. Indeed, the ability of a wound to heal with minimal scar formation can have a profound effect on the patient and on medical or surgical practice.

In one embodiment, the composition of the invention is effective against burn. There are various types of burn such as thermally induced burns, thermally induced controlled burns, chemical burns, radiation burns, electrical burns, ice burns, or burns caused by exposure to lightening that may be prevented and/or treated with the compositions and methods of the present invention. There are various degrees of burns including those that are 1st degree, 2nd degree, 3rd degree, or 4th degree burns or any combination thereof.

By preventing and/or treating and/or ameliorating inflammation, it is possible to inhibit the complex chemical changes, which often become the determining factors in a patient's outcome. The composition of the present invention curtails these chemical changes making the body react the way it would after a lesser trauma such as a mild wound or cut instead of a more serious wound. After a mild cut or wound, the body begins to clog the wound with platelets so the healing stage can begin. This is a normal response that promotes repair of the injured area.

In another embodiment, the compositions and methods of the present invention directly or indirectly prevent microorganisms from invading the wound site by promoting wound healing. Patients will therefore also suffer less because they remain free from various infections commonly associated with typical wound. The composition thus prevents wound injuries from progressing to greater severity. The use of compositions and methods of the present invention prevents, treats and/or ameliorates the tissue damage that is the breeding ground for microorganisms in most wounds. The ability to interfere with the cycle of infection can halt the disease process. The reduced rate of infection translates to reduced severity of disease, disorders and deformities that are normal consequences of a wound. Gram-positive and gram-negative bacteria infections usually develop after a wound. The destructive consequences of these pathophysiological phases are related to MOD (Multiple Organ Dysfunction) at an early stage. The translocation of microorganisms can be prevented if the area of plasma leakage can be blocked.

In one embodiment, the compositions of the present invention prevent the accumulation of neutrophils, and their release of oxygen free radicals and various proteases by limiting inflammation, thereby prohibiting further tissue damage.

In another embodiment, the composition of the invention is used to directly or indirectly prevent and/or treat numerous wound Associated Disease Responses (ADR's). A list of the typical ADRs includes, but is not limited to, compartment syndrome, acidosis, acute renal failure, acute tubular necrosis, cellulitis, secondary seizures, contractures, reduced end-organ perfusion, endotoxemia, exotoxemia, gangrene, nosocomial pneumonia (50% of patients with burn/smoke inhalation injury develop this type), ARDS (acute respiratory distress syndrome), ventilator associated pneumonia, sepsis, septic shock, thromboembolic complications, and those other wound associated diseases with an inflammatory component such as, but not limited to, anemia, cancer, congestive heart failure, reduced end-organ perfusion, dermatomyositis (DM), dermatitis, alveolar proteinosis pneumonia, bronchcolotis obliterans organizing pneumonia (BOOP), chronic aspiration lipoid pneumonia, community acquired pneumonia (CAP), coronavirus pneumonia, cryptoccal pneumonia, chlamydia pneumonia, desquamative interstitial pneumonia, eosinophilic pneumonia, haemophilus influenza pneumonia, haemophilus pneumonia, haemophilus parainfluenzae pneumonia, idiopathic pneumonia, influenza associated pneumonia, idiopathic interstitial pneumonia, kliebsiella pneumonia, mycoplasma pneumonia, non-specific interstitial pneumonia (associated with dermatomyositis-DM), pasteurella multocida pneumonia, pneumocystis carinnii-(PCP) pneumonia, pseudomonas aeruginosa pneumonia, respiratory synctial virus infection, staphylococcal necrotising pneumonia, tuberculosis pneumonia, usual interstitial pneumonitis (UIP), varicella zoster virus pneumonia, toxic shock syndrome, and toxic epidermal necrosis (TEN).

Other conditions related to wounds or sores which may be successfully treated or prevented according to the invention are, by way of example and not limitation, anthrax wounds, tetanus, gas gangrene, scalatina, erysipelas, sycosis barbae, folliculitis, impetigo contagiosa, or impetigo bullosa, etc.

In another embodiment, the compositions and methods of the present invention comprising $\alpha,\beta$ unsaturated benzyl styryl sulfones and functional derivatives thereof are useful to treat the pain associated with and/or prevent a disease or disorder often accompanying a wound or damaged tissue wherein said disease or disorder is selected from the group consisting of: myocardial ischemia, tissue and muscle-associated ischemia, extremity-associated ischemia, stroke, sepsis, amyotrophic lateral sclerosis (ALS), seizures, extension of strokes after initial tissue damage, functional brain damage secondary to primary and secondary brain tumors, local brain damage secondary to meningitis or brain abscess, viral meningitis, viral encephalitis, and/or local brain damage secondary to trauma, transplantation of organs or tissue, graft-versus-host diseases brought about by transplantation, autoimmune syndromes including rheumatoid arthritis, systemic lupus erythematosus, Hashimoto's thyroiditis, multiple sclerosis, myasthenia gravis, type I diabetes mellitus, juvenile-onset or recent-onset diabetes mellitus, posterior uveitis, allergic encephalomyelitis, glomerulonephritis, post-infectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, Lichen planus, Pemphigus, bullous pemphigoid, Epidermolysis bullosa, urticaria, angioedemas, vasculitis, erythema, cutaneous eosinophilia, Lupus erythematosus, acne, Alopecia greata, keratoconjunctivitis, vernal conjunctivitis, uveitis associated with Behcet's disease, keratitis, herpetic keratitis, dystrophia epithelialis corneae, ocular pemphigus, Mooren's ulcer, Scleritis, Graves' opthalmopathy, Vogt-Koyanagi-Harada syndrome, sarcoidosis, gastric ulcers, vascular damage caused by ischemic diseases and thrombosis, ischemic bowel diseases, inflammatory bowel diseases, necrotizing enterocolitis, intestinal lesions associated with thermal burns, Celrac diseases, proctitis, eosinophilic gastroenteritis, mastocytosis, Crohn's disease, ulcerative colitis, rhinitis, eczema, interstitial nephritis, Goodpasture's syndrome, hemolytic-uremic syndrome, diabetic nephropathy, myositis, Guillain-Barre syndrome, polyneuritis, mononeuritis, radiculopathy, osteoporosis, sarcoidosis, fibroid lung, idiopathic interstitial pneumonia, dermatomyositis, photoallergic sensitivity, cutaneous T cell lymphoma, atherosclerosis, aortitis syndrome, polyarteritis nodosa, myocardosis, scleroderma, Wegener's granulomatosis, Sjogren's syndrome, eosinophilic fascitis, lesions of gingiva, ischemia-reperfusion injury of organs, endotoxin-shock, pseudomembranous colitis, colitis caused by drug or radiation, ischemic acute renal insufficiency, chronic renal insufficiency, lung cancer, pulmonary emphysema, dermatitis erythema multiforme, linear IgA ballous dermatitis, carcinogenesis, metastasis of carcinoma, primary biliary cirrhosis, sclerosing cholangitis, partial liver resection, acute liver necrosis, necrosis caused by toxin, viral hepatitis, cirrhosis, alcoholic cirrhosis, augmentation of chemotherapeutic effect, cytomegalovirus infection, cancer, trauma, and chronic bacterial infection.

Representative examples of $\alpha,\beta$ unsaturated benzyl styryl sulfones or functional derivatives thereof that may be used in the prophylactic and therapeutic methods for treating localized and systemic inflammation associated with wounds include, for example, but not limited to, pharmaceutical compositions comprising one or more of the following compounds, that may be used alone or in combination with a secondary active or inactive drug (e.g., antibacterial, pain killer, antiviral, and any combinations thereof among others.

Thus, in one aspect the present invention provides methods for treating wounds or damaged tissues comprising administering to a wound or damaged tissues of a subject in need thereof a therapeutically effective amount of a composition comprising a compound of the α,β-unsaturated aryl sulfone or a functional derivative thereof and a pharmaceutically acceptable carrier or diluent.

According to one embodiment, the α,β unsaturated aryl sulfone group is a styryl sulfone group wherein the hydrogen atoms attached to the α and β carbons are optionally replaced by other chemical groups, and the phenyl ring is optionally substituted. The α,β unsaturated aryl sulfone wound healing compounds are characterized by cis-trans isomerism resulting from the presence of a double bond. Stearic relations around a double bond are designated as "Z" or "E". Both configurations are included in the scope of "α,β unsaturated aryl sulfone":

According to one embodiment, the α,β unsaturated aryl sulfone compound is a compound of the formula I:

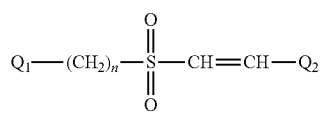

I wherein: n is one or zero;

Q1 and Q2 are, same or different, are substituted or unsubstituted aryl, or substituted or unsubstituted heteroaryl.

Preferably, n in formula I is one, that is, the compounds comprise α,β unsaturated benzylsulfones, e.g. styryl benzylsulfones.

In one preferred embodiment according to formula I, Q1 and/or Q2 are selected from substituted and unsubstituted heteroaryl; for example, (E)-3-furanethenyl-2,4-dichlorobenzylsulfone. In another preferred embodiment according to formula I, Q1 and Q2 are selected from substituted and unsubstituted phenyl.

Preferred compounds where Q1 and Q2 are selected from substituted and unsubstituted phenyl comprise compounds of the formula II:

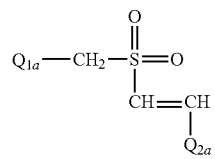

II wherein:

Q1a and Q2a are independently selected from the group consisting of phenyl and mono-, di-, tri-, tetra- and penta-substituted phenyl where the substituents, which may be the same or different, are independently selected from the group consisting of hydrogen, halogen, C1-C8 alkyl, C1-C8 alkoxy, nitro, cyano, carboxy, hydroxy, phosphonato, amino, sulfamyl, acetoxy, dimethylamino(C2-C6 alkoxy), C1-C6 trifluoroalkoxy and trifluoromethyl.

In one embodiment, compounds of formula II are at least di-substituted on at least one ring, that is, at least two substituents on at least one ring are other than hydrogen. In another embodiment, compounds of formula II are at least trisubstituted on at least one ring, that is, at least three substituents on at least one ring are other than hydrogen.

In another embodiment, the wound healing compound has the formula III:

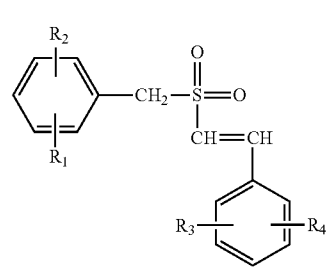

III wherein R1, R2, R3 and R4 are independently selected from the group consisting of hydrogen, halogen, C1-C8 alkyl, C1-C8 alkoxy, nitro, cyano, carboxy, hydroxy phosphonato, amino, sulfamyl, acetoxy, dimethylamino(C2-C6 alkoxy), C1-C6 trifluoroalkoxy and trifluoromethyl.

According to a particularly preferred embodiment of the invention, the wound healing compound is according to formula III, and R1 and R2 are independently selected from the group consisting of hydrogen, halogen, cyano, and trifluoromethyl; and R3 and R4 are independently selected from the group consisting of hydrogen and halogen. According to one sub-embodiment of formula III, the wound healing α,β unsaturated aryl sulfone compound is a compound of the formula IIIa, wherein R2 and R4 are other than hydrogen:

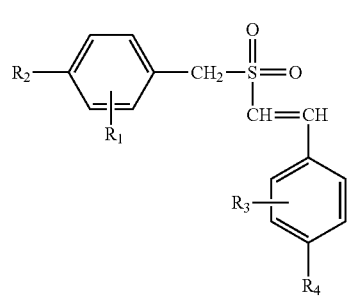

IIIa

Preferred compounds according to formula IIIa having the E-configuration include, but are not limited to, (E)-4-fluorostyryl-4-chlorobenzylsulfone; (E)-4-chlorostyryl-4-chlorobenzylsulfone; (E)-2-chloro-4-fluorostyryl-4-chlorobenzylsulfone; (E)-4-carboxystyryl-4-chlorobenzyl sulfone; (E)-4-fluorostyryl-2,4-dichlorobenzylsulfone; (E)-4-fluorostyryl-4-bromobenzylsulfone; (E)-4-chlorostyryl-4-bromobenzylsulfone; (E)-4-bromostyryl-4-chlorobenzylsulfone; (E)-4-fluorostyryl-4-trifluoromethylbenzylsulfone; (E)-4-fluorostyryl-3,4-dichlorobenzylsulfone; (E)-4-fluorostyryl-4-cyanobenzylsulfone; (E)-2,4-dichloro-4-chlorobenzylsulfone; (E)-4-fluorostyryl-4-chlorophenylsulfone and (E)-4-chlorostyryl-2,4-dichlorobenzylsulfone.

According to another embodiment, compounds of formula IIIa have the Z configuration wherein R1 and R3 are hydrogen, and R2 and R4 are selected from the group consisting of 4-halo. Such compounds include, for example, (Z)-4-chlorostyryl-4-chlorobenzylsulfone; (Z)-4-chlorostyryl-4-fluorobenzylsulfone; (Z)-4-fluorostyryl-4-chlorobenzylsulfone; (Z)-4-bromostyryl-4-chlorobenzylsulfone; and (Z)-4-bromostyryl-4-fluorobenzylsulfone.

A preferred compound of Formula III is formula III B

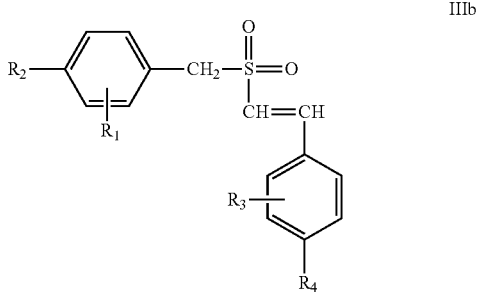

IIIb wherein R1 and R3 are hydrogen, R2 is halogen and R4 is carboxy and the stearic configuration around the double bond is E.

In another preferred embodiment of the invention, R1 and R3 are hydrogen, R2 is chlorine and R4 is carboxy and the stearic configuration around the double bond is E, e.g. (E)-4-carboxystyryl-4-chlorobenzyl sulfone (ON 1210).

According to another embodiment, the wound healing α,β unsaturated aryl sulfone compound is a compound of the formula IV:

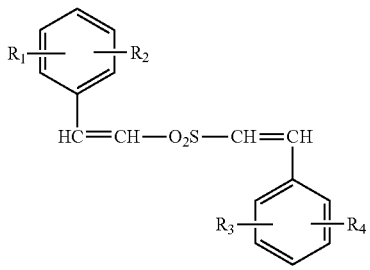

IV wherein
R1, R2, R3, and R4 are independently selected from the group consisting of hydrogen, halogen, C1-8 alkyl, C1-8 alkoxy, nitro, cyano, carboxy, hydroxy, and trifluoromethyl.

In one embodiment, R1 in formula IV is selected from the group consisting of hydrogen, chlorine, fluorine and bromine; and R2, R3 and R4 are hydrogen. A preferred compound of formula IV is (Z)-styryl-(E)-2-methoxy-4-ethoxystyrylsulfone.

According to yet another embodiment, the wound healing α,β unsaturated aryl sulfone compound is a compound of the formula V:

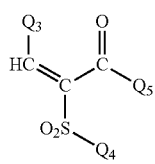

V wherein
Q3, Q4 and Q5 are independently selected from the group consisting of phenyl and mono-, di-, tri-, tetra- and penta-substituted phenyl where the substituents, which may be the same or different, are independently selected from the group consisting of halogen, C1-C8 alkyl, C1-C8 alkoxy, nitro, cyano, carboxy, hydroxy, amino, sulfamyl, acetoxy, dimethylamino(C2-C6 alkoxy), C1-C6 trifluoroalkoxy and trifluoromethyl.

According to one sub-embodiment of formula V, the wound healing α,β unsaturated aryl sulfone compound is a compound of the formula Va:

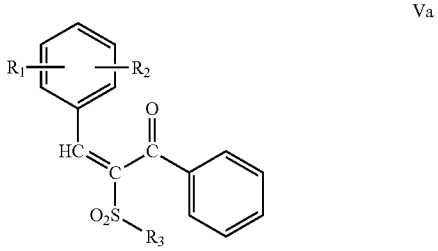

Va wherein
R1 and R2 are independently selected from the group consisting of hydrogen, halogen, C1-C8 alkyl, C1-8 alkoxy, nitro, cyano, carboxyl, hydroxyl, and trifluoromethyl; and R3 is selected from the group consisting of unsubstituted phenyl, mono-substituted phenyl and di-substituted phenyl, the substituents on the phenyl ring being independently selected from the group consisting of halogen and C1-8 alkyl.

Preferably, R1 in formula V is selected from the group consisting of fluorine and bromine; R2 is hydrogen; and R3 is selected from the group consisting of 2-chlorophenyl, 4-chlorophenyl, 4-fluorophenyl, and 2-nitrophenyl.

Another wound healing styryl sulfone according to formula V is the compound wherein R1 is fluorine, R2 is hydrogen and R3 is phenyl, that is, the compound 2-(phenylsulfonyl)-1-phenyl-3-(4-fluorophenyl)-2-propen-1-one. Where a substituent on an aryl nucleus is an alkoxy group, the carbon chain may be branched or straight, with straight being preferred. Preferably, the alkoxy groups comprise C1-C6 alkoxy, more preferably C1-C4 alkoxy, most preferably methoxy.

The α,β-unsaturated aryl sulfones may take the form of pharmaceutically acceptable salts. The term "pharmaceutically acceptable salts" embraces salts commonly used to form alkali metal salts and to form addition salts of free acids or free bases. A preferred salt useful in the formulation is the sodium salt (ON 1210 Na).

Certain derivatives of compounds of formula (I-V) which may have little or no pharmacological activity themselves can, when administered into or onto the body, be converted into compounds of formula (I-V) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

In one embodiment, the prodrug is a compound that is transformed in vivo to yield a compound of Formula (I-V) or a pharmaceutically acceptable salt or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S Symposium Series, and in Bioreversible Carriers in Drug Design, ed. Edward B. Roche, American Pharmaceutical Association and Pergamon Press, 1987.

Prodrugs in accordance with the invention can, for example, be produced by replacing appropriate functionalities present in the compounds of Formula (I-V) with certain moieties known to those skilled in the art as 'pro-moieties' as described, for example, in "Design of Prodrugs" by H Bundgaard (Elsevier, 1985).

Moreover, certain compounds of Formula (I-V) may themselves act as prodrugs of other compounds of Formula (I-V).

A prodrug of a compound of Formula (I-V) may be one formed in a conventional manner with a functional group of the compound, such as with an amino, hydroxy or carboxy group.

For example, if a compound of the present invention incorporates an amine functional group, a prodrug can be formed by the replacement of a hydrogen atom in the amine group with a group such as R-carbonyl, RO-carbonyl, NRR'-carbonyl where R and R' are each independently (C1-C10)alkyl, (C3-C7)cycloalkyl, benzyl, or R-carbonyl is a natural alpha-aminoacyl or natural alpha-aminoacyl-natural alpha-aminoacyl, —C(OH)C(O)OY' wherein Y' is H, (C1-C6)alkyl or benzyl, —C(OYd)Y1 wherein Yd is (C1-C4) alkyl and Y1 is (C1-C6)alkyl, carboxy(C1-C6)alkyl, amino(C1-C4)alkyl or mono-N— or di-N,N—(C1-C6)alkylaminoalkyl, —C(Y2)Y3 wherein Y2 is H or methyl and Y3 is mono-N— or di-N,N—(C1-C6)alkylamino, morpholino, piperidin-1-yl or pyrrolidin-1-yl.

Similarly, if a compound of the present invention contains an alcohol functional group, a prodrug can be formed by the replacement of the hydrogen atom of the alcohol group with a group such as (C1-C6)alkanoyloxymethyl, 1-((C1-C6)alkanoyloxy)ethyl, 1-methyl-1-((C1-C6)alkanoyloxy)ethyl, (C1-C6)alkoxycarbonyloxymethyl, N—(C1-C6)alkoxycarbonylaminomethyl, succinoyl, (C1-C6)alkanoyl, .alpha.-amino(C1-C4)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —P(O)(O(C1-C6)alkyl) 2 or glycosyl (the radical resulting from the removal of a hydroxyl group of the hemiacetal form of a carbohydrate).

If a compound of the present invention contains a carboxylic acid functional group, a prodrug can comprise an ester formed by the replacement of the hydrogen atom of the acid group with a group such as (C1-C8)alkyl, (C2-C12)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C1-C2)alkylamino(C2-C3)alkyl (such as beta-dimethylaminoethyl), carbamoyl-(C1-C2)alkyl, N,N-di(C1-C2)alkylcarbamoyl-(C1-C2)alkyl and piperidino-, pyrrolidino- or morpholino(C2-C3)alkyl.

Also included within the scope of the invention are metabolites of compounds of Formula (I-V) that are compounds formed in vivo upon administration of the drug. Some examples of metabolites in accordance with the invention include: (i) where the compound of Formula (I-V) contains a methyl group, an hydroxymethyl derivative thereof (—CH3→—CH2OH); (ii) where the compound of Formula (I-V) contains a tertiary amino group, a secondary amino derivative thereof (—NR1R2→—NHR1 or —NHR2); (iii) where the compound of formula (I) contains a secondary amino group, a primary derivative thereof (—NHR1→—NH2); (iv) where the compound of Formula (I-V) contains a phenyl moiety, a phenol derivative thereof (-Ph→-PhOH); and (v) where the compound of Formula (I-V) contains an amide group, a carboxylic acid derivative thereof (—CONH2→—COOH).

Further examples of replacement groups in accordance with the foregoing examples and examples of other prodrug types in accordance with the invention may be found in the aforementioned references.

Compounds of the invention may exist in various hydrated forms. For example, the compounds of the present invention may exist in unsolvated as well as solvated forms with pharmaceutically acceptable solvents such as water, ethanol, and the like, and it is intended that the invention embrace both solvated and unsolvated forms.

The compounds of the present invention may have the ability to crystallize in more than one form, a characteristic known as polymorphism, and all such polymorphic forms ("polymorphs") are encompassed within the scope of the invention.

Alternatively, the compounds of the invention may be in an amorphous state.

Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as 2H, 3H, 11C, 13C, 14C, 13N, 15N, 15O, 17O, 18O, 31P, 32P, 35S, 18F, 123I, 125I and 36Cl, respectively.

Certain isotopically-labeled compounds of the present invention (e.g., those labeled with 3H and 14C) are useful in compound and/or substrate tissue distribution assays. Tritiated (i.e., 3H) and carbon-14 (i.e., 14C) isotopes are particularly preferred for their ease of preparation and detectability. Further, substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Positron emitting isotopes such as 15O, 13N, 11C, and 18F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

When one or more chiral centers are present in the compounds of the present invention, the individual isomers and mixtures thereof (e.g., racemates, racemic mixtures, individual diastereomers or enantiomers, etc.) are intended to be encompassed by the formulae depicted herein. Thus, for example, the exemplified compounds disclosed herein are depicted as specific stereoisomers. It should be understood that the present invention includes such compounds but having alternate stereochemistry at one or more of the chiral centers.

In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

In certain embodiments, compounds of the invention may exist in several tautomeric forms. Accordingly, the chemical structures depicted herein encompass all possible tautomeric forms of the illustrated compounds. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

Methods of Use

Thus, in its simplest aspect, the present invention provides methods for treatment of wounds, and for preventing or treating symptoms of diseases and/or conditions ensuing from the wound by administration of a compound of α,β-unsaturated aryl sulfones and in particular a compound of α,β-unsaturated benzyl styryl sulfones.

In one aspect, the present invention relates to methods of controlling or alleviating pain by reducing the severity of inflammation associated with a wound or damaged tissues comprising administering to a subject in need thereof a therapeutically effective amount of a pharmaceutical composition comprising compound of α,β-unsaturated aryl sulfones and in particular a compound of α,β-unsaturated benzyl styryl sulfones, or a functional derivative thereof; and a pharmaceutically acceptable carrier or diluents.

The present invention also relates to a method for promoting rapid healing and/or regeneration of damaged tissues resulting from a wound or disease comprising administering to a subject in need thereof a therapeutically effective amount of a pharmaceutical composition comprising a compound of α,β-unsaturated aryl sulfones, and in particular a compound of α,β-unsaturated benzyl styryl sulfones, or a functional derivative thereof; and a pharmaceutically acceptable excipient, wherein said pharmaceutical composition promotes rapid healing and/or regeneration of damaged tissues while retaining the original composition of the tissue and minimizing complications and scarring.

In one aspect of the invention, a method is provided for ameliorating the diseases associated with inflammatory mediators and the systemic response to a wound or tissue injury. The initial inflammation and edema accompanying a wound or tissue injury involves oxidant and arachidonic acid metabolites, which trigger neutrophils and macrophages to release cytokines, including, but not limited to, tumor necrosis factor, IL-1, IL-2, IL-8, IL-12, IL-18, as well as nitric oxide. Endotoxins from pathogens in the wound and/or the gastrointestinal tract initiate and enhance inflammation and can result in the translocation of microorganisms across the gut and generate pathology at distant sites which would otherwise be unaffected by the trauma. The septic response is caused by excessive inflammatory mediators derived from the host, especially IL-1, IL-2, TNF, IL-8, NO, reactive oxygen intermediates (ROI), and its complications. These complications or "associated disease responses" (ADRs) are caused by edema, inflammation, and the translocation of microbial flora.

In yet another aspect, the present invention relates to a method for preventing or ameliorating the deleterious inflammatory response associated with controlled therapeutic thermal induced skin damage employed in the use of lasers for the treatment of medical conditions and the use of induced thermal injury in various cosmetic procedures comprising administering to a subject in need thereof a therapeutically effective amount of a pharmaceutical composition comprising a compound of α,β-unsaturated aryl sulfones, and in particular a compound of α,β-unsaturated benzyl styryl sulfones, or a functional derivative thereof, and a pharmaceutically carrier or diluent, wherein said pharmaceutical composition prevents or ameliorates the deleterious inflammatory response and/or the adverse effects associated with such controlled therapeutic thermal induced skin damage.

In another aspect, the present invention also relates to a method for preventing or ameliorating the adverse affects associated with controlled thermal induced skin damage employed in scar and tattoo removal, cancer excisions, cautery excision of polyps, ulcers, treatment of decubitus ulcers (bedsores), acne, cutaneous fungal infections comprising administering to a subject in need thereof a therapeutically effective amount of a pharmaceutical composition comprising a compound of α,β-unsaturated aryl sulfones, and in particular a compound of α,β-unsaturated benzyl styryl sulfones, or a functional derivative thereof, and a pharmaceutically acceptable excipient, wherein said pharmaceutical composition promotes rapid regeneration of damaged tissues while retaining the original composition of the tissue and minimizing complications and scarring associated with the thermally induced burn in one or more of the recited conditions.

In yet another aspect, the present invention relates to methods of preventing or ameliorating blistering or pain associated with overexposure to sun comprising administering to a subject in need thereof a therapeutically effective amount of a pharmaceutical composition comprising a compound of α,β-unsaturated aryl sulfones, and in particular a compound of α,β-unsaturated benzyl styryl sulfones, or a functional derivative thereof, and a pharmaceutically acceptable carrier or diluent.

In yet another aspect of the invention, a method is provided for limiting intramolecular nucleophilic reactions that occur in most pathways that affects the reactivity of intramolecular and intermolecular groups comprising administering to a patient in need thereof a therapeutically effective amount of a pharmaceutical composition comprising a compound of α,β-unsaturated aryl sulfones, and in particular a compound of α,β-unsaturated benzyl styryl sulfones, or a functional derivative thereof; and a pharmaceutically acceptable carrier or diluent. A number of oxygen groups or ROI are unstable in wound injuries and treatment with the composition of the invention will inhibit these oxygen free radicals or oxidants.

In each of the aforementioned aspects and embodiments of the invention, combination therapies with other active drugs are also specifically contemplated herein. In particular, the compositions of the present invention may be administered with one or more macrolide or non-macrolide antibiotics, antibacterial agents, antifungal agents, antiviral agents, antiparasitic agents, and/or antiinflammatory or immunomodulatory drugs or agents.

Examples of macrolide antibiotics that may be used in combination with the composition of the present invention include, inter alia, the following synthetic, semi-synthetic or naturally occurring microlidic antibiotic compounds: methymycin, neomethymycin, YC-17, litorin, erythromycin A to F, oleandomycin, roxithromycin, dirithromycin, flurithromycin, clarithromycin, davercin, azithromycin, josamycin, kitasamycin, spiramycin, midecamycin, rokitamycin, miokamycin, lankacidin, and the derivatives of these compounds. Thus, erythromycin and compounds derived from erythromycin belong to the general class of antibiotics known as "macrolides." Examples of preferred erythromycin and erythromycin-like compounds include: erythromycin, clarithromycin, azithromycin, and troleandomycin.

Additional antibiotics, other than the macrolidic antibiotics described above, which are suitable for use in the methods of the present invention include, for example, any molecule that tends to prevent, inhibit or destroy life and as such, and as used herein, includes antibacterial agents, antifungal agents, antiviral agents, and antiparasitic agents. These agents may be isolated from an organism that produces the agent or procured from a commercial source Anti-bacterial antibiotic agents include, but are not limited to, penicillins, cephalosporins, carbacephems, cephamycins, carbapenems, monobactams, aminoglycosides, glycopeptides, quinolones, tetracyclines, macrolides, oxazalidiinones, streptogramins, and fluoroquinolones. Examples of antibiotic agents include, but are not limited to, linezolid (Zyvax), dalfopristine, quinupristine, Penicillin G (CAS Registry No.: 61-33-6); Methicillin (CAS Registry No.: 61-32-5); Nafcillin (CAS Registry No.: 147-52-4); Oxacillin (CAS Registry No.: 66-79-5); Cloxacillin (CAS Registry No.: 61-72-3); Dicloxacillin (CAS Registry No.: 3116-76-5); Ampicillin (CAS Registry No.: 69-53-4); Amoxicillin (CAS Registry No.: 26787-78-0); Ticarcillin (CAS Registry No.: 34787-01-4); Carbenicillin (CAS Registry No.: 4697-36-3); Mezlocillin (CAS Registry No.: 51481-65-3); Azlocillin (CAS Registry No.: 37091-66-0); Piperacillin (CAS Registry No.: 61477-96-1); Imipenem (CAS Registry No.: 74431-23-5); Aztreonam (CAS Registry No.: 78110-38-0); Cephalothin (CAS Registry No.: 153-61-7); Cefazolin (CAS Registry No.: 25953-19-9); Cefaclor (CAS Registry No.: 70356-03-5); Cefamandole formate sodium (CAS Registry No.: 42540-40-9); Cefoxitin (CAS Registry No.: 35607-66-0); Cefuroxime (CAS Registry No.: 55268-75-2); Cefonicid (CAS Registry No.: 61270-58-4); Cefinetazole (CAS Registry No.: 56796-20-4); Cefotetan (CAS Registry No.: 69712-56-7); Cefprozil (CAS Registry No.: 92665-29-7); Loracarbef (CAS Registry No.: 121961-22-6); Cefetamet (CAS Registry No.: 65052-63-3); Cefoperazone (CAS Registry No.: 62893-19-0); Cefotaxime (CAS Registry No.: 63527-52-6); Ceftizoxime (CAS Registry No.: 68401-81-0); Ceftriaxone (CAS Registry No.: 73384-59-5); Ceftazidime (CAS Registry No.: 72558-82-8); Cefepime (CAS Registry No.: 88040-23-7); Cefixime (CAS Registry No.: 79350-37-1); Cefpodoxime (CAS Registry No.: 80210-62-4); Cefsulodin (CAS Registry No.: 62587-73-9); Fleroxacin (CAS Registry No.: 79660-72-3); Nalidixic acid (CAS Registry No.: 389-08-2); Norfloxacin (CAS Registry No.: 70458-96-7); Ciprofloxacin (CAS Registry No.: 85721-33-1); Ofloxacin (CAS Registry No.: 82419-36-1); Enoxacin (CAS Registry No.: 74011-58-8); Lomefloxacin (CAS Registry No.: 98079-51-7); Cinoxacin (CAS Registry No.: 28657-80-9); Doxycycline (CAS Registry No.: 564-25-0); Minocycline (CAS Registry No.: 10118-90-8); Tetracycline (CAS Registry No.: 60-54-8); Amikacin (CAS Registry No.: 37517-28-5); Gentamicin (CAS Registry No.: 1403-66-3); Kanamycin (CAS Registry No.: 8063-07-8); Netilmicin (CAS Registry No.: 56391-56-1); Tobramycin (CAS Registry No.: 32986-56-4); Streptomycin (CAS Registry No.: 57-92-1); Azithromycin (CAS Registry No.: 83905-01-5); Clarithromycin (CAS Registry No.: 81103-11-9); Erythromycin (CAS Registry No.: 114-07-8); Erythromycin estolate (CAS Registry No.: 3521-62-8); Erythromycin ethyl succinate (CAS Registry No.: 41342-53-4); Erythromycin glucoheptonate (CAS Registry No.: 23067-13-2); Erythromycin lactobionate (CAS Registry No.: 3847-29-8); Erythromycin stearate (CAS Registry No.: 643-22-1); Vancomycin (CAS Registry No.: 1404-90-6); Teicoplanin (CAS Registry No.: 61036-64-4); Chloramphenicol (CAS Registry No.: 56-75-7); Clindamycin (CAS Registry No.: 18323-44-9); Trimethoprim (CAS Registry No.: 738-70-5); Sulfamethoxazole (CAS Registry No.: 723-46-6); Nitrofurantoin (CAS Registry No.: 67-20-9); Rifampin (CAS Registry No.: 13292-46-1); Mupirocin (CAS Registry No.: 12650-69-0); Metronidazole (CAS Registry No.: 443-48-1); Cephalexin (CAS Registry No.: 15686-71-2); Roxithromycin (CAS Registry No.: 80214-83-1); Co-amoxiclavuanate; combinations of Piperacillin and Tazobactam; and their various salts, acids, bases, and other derivatives.

Antifungal agents include, but are not limited to, terbinafine hydrochloride, nystatin, amphotericin B, griseofulvin, ketoconazole, miconazole nitrate, flucytosine, fluconazole, itraconazole, clotrimazole, benzoic acid, salicylic acid, voriconazole, caspofungin, and selenium sulfide.

Antiviral agents include, but are not limited to, amantadine hydrochloride, rimantadin, acyclovir, famciclovir, foscarnet, ganciclovir sodium, idoxuridine, ribavirin, sorivudine, trifluridine, valacyclovir, vangancyclovir, pencyclovir, vidarabin, didanosine, stavudine, zalcitabine, zidovudine, interferon alpha, and edoxudine.

Antiparasitic agents include, but are not limited to, pirethrins/piperonyl butoxide, permethrin, iodoquinol, metronidazole, diethylcarbamazine citrate, piperazine, pyrantel pamoate, mebendazole, thiabendazole, praziquantel, albendazole, proguanil, quinidine gluconate injection, quinine sulfate, chloroquine phosphate, mefloquine hydrochloride, primaquine phosphate, atovaquone, co-trimoxazole (sulfamethoxazole/trimethoprim), and pentamidine isethionate.

In another aspect, in the method of the present invention, one may, for example, supplement the composition by administration of a therapeutically effective amount of one or more an antiinflammatory or immunomodulatory drugs or agents. By "immunomodulatory drugs or agents", it is meant, e.g., agents which act on the immune system, directly or indirectly, e.g., by stimulating or suppressing a cellular activity of a cell in the immune system, e.g., T-cells, B-cells, macrophages, or other antigen presenting cells (APC), or by acting upon components outside the immune system which, in turn, stimulate, suppress, or modulate the immune system, e.g., hormones, receptor agonists or antagonists, and neurotransmitters; immunomodulators can be, e.g., immunosuppressants or immunostimulants.

Antiinflammatory or immunomodulatory drugs or agents suitable for use in this invention include, but are not limited to, interferon derivatives, e.g., betaseron, .beta.-interferon; prostane derivatives, iloprost, cicaprost; glucocorticoid, e.g., cortisol, prednisolone, methylprednisolone, dexamethasone; immunsuppressives, e.g., cyclosporine A, FK-506, methoxsalene, thalidomide, sulfasalazine, azathioprine, methotrexate; lipoxygenase inhibitors, e.g., zileutone, leukotriene antagonists, prostaglandins, peptide derivatives, e.g., ACTH and analogs; IL-1 receptor antagonists, IL-18 binding protein, activated protein C (Xigris), soluble TNF-receptors; TNF-antibodies; soluble receptors of interleukins, other cytokines, T-cell-proteins; antibodies against receptors of interleukins, other cytokines, and T-cell-proteins (the text of each of the aforementioned references is expressly incorporated by reference herein).

Additional Uses

The present invention also has applications in emergency kits outfitted to contain a pharmaceutical composition comprising α,β unsaturated benzyl styryl sulfones or a functional derivative thereof, available for use in every emergency first aid kit. In one embodiment, a topical formulation of the composition of the invention can be applied to the skin immediately after an accident or injury. For example, such emergency kits would be invaluable in each household for use in emergency household accidents, in the car, including residential vehicles, commercial vehicles, and most emergency response and police vehicles.

The present invention also has applications in all types of sunburn and would be employed in pre- and/or post-sun exposure care to prevent skin cancer, prevent blistering, sooth, cool and reduce/eliminate the pain of sunburns. The present invention also has applications in artificial sun tanning salons.

The present invention also has applications in all fields of professional uses including for example, hospitals, emergency and burn treatment, doctor office, general practitioner's office, ambulances and emergency vehicles, high risk industries, fire fighting, military, navy, law enforcement, mechanical workshops, auto repair, welding, restaurants, etc.

The present pharmaceutical composition is effective in human, mice and other mammals, such as veterinary animals including, without limitation, dogs, cats, other household pets, horses, farm animals, and the like.

Pharmaceutical Composition Formulation, Dosage and Mode of Administration

The present invention also provides pharmaceutical compositions comprising a therapeutically effective amount of an α,β-unsaturated aryl sulfone compound, and a pharmaceutically acceptable carrier. The pharmaceutical composition also refers to a composition that additionally contains one or more active or inactive agents.

According to one embodiment, the composition of the invention having wound healing activity as described are provided as isolated and substantially purified compounds in pharmaceutically acceptable formulations. These formulations can be administered by standard routes.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In one embodiment, the compositions described herein, are aqueous-based, although ethanol is also a preferred base-component of the formulations described herein.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. In one embodiment, the composition is formulated as a suppository, with traditional binders and carriers such as triglycerides.

The composition of the invention can be formulated as neutral or salt forms. As used herein, by "pharmaceutically acceptable salt" it is meant those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylaminoethanol, histidine, procaine, etc. The salts can be prepared in situ during the final isolation and purification of the compounds of the invention, or separately by reacting the free base function with a suitable organic acid. Representative acid addition salts include acetate, adipate, alginate, ascorbate, aspartate, benzene-sulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary as ammonium, and mine cations, including, but not limited to ammonium, tetramethylammonium, tetraethylammonium, methylamine, dimethylamine, trimethylamine, triethylamine, ethylamine, and the like.

In one embodiment, the composition of the present invention is intended to be applied topically and directly to the wound. In this embodiment, the composition is in the form of an ointment, salve or cream which is spread directly onto the wound and then covered with a standard sterile dressing pad or other appropriate dressing material. Alternatively, the ointment, cream or salve of the present composition is applied directly onto the dressing pad or other appropriate dressing material.

The preferred routes of administration of the compositions described herein include, for example, parenteral, nasal, topical (including buccal and sublingual) and oral administration.

Parenteral administration includes intravenous, intramuscular, intraarterial, intraperitoneal, intravaginal, intravesical (e.g., into the bladder), intradermal, intracranial, intratracheal and epidural) administration. The compounds of the invention comprising a compound of $\alpha,\beta$-unsaturated benzylsulfone (e.g. ON 01210.Na) in combination with at least one stabilizing agent and a pharmaceutically acceptable carrier. ON 01210.Na in such formulations may comprise from 0.1 to 99.99 weight percent. By "pharmaceutically acceptable carrier" is meant any carrier, diluent or excipient, for example a water soluble polymer/cosolvent, which is compatible with the other ingredients of the formulation and is not deleterious to the subject.

Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In yet another embodiment, the composition is formulated for intravenous administration to human beings. Typically, compositions for intravenous administration are solutions in sterile isotonic aqueous buffer. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In addition, the composition of the invention may be incorporated into biodegradable polymers allowing for sustained release of the compound, the polymers being implanted in the vicinity of where drug delivery is desired, for example, at the site of a wound, so that the composition is slowly released systemically. Osmotic mini-pumps may also be used to provide controlled delivery of high concentrations of the composition of the invention through cannulae to the site of interest, such as directly into a tissue that is damaged. The biodegradable polymers and their use are described, for example, in detail in Brem et al., J. Neurosurg. 74:441-446 (1991), which is hereby incorporated by reference in its entirety.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Pharmaceutically acceptable sterile aqueous or non-aqueous solutions include, by way of example and not limitation, dispersions, suspensions, or emulsions as well as sterile powders for reconstitution into sterile injectable solutions or dispersions just prior to use. Examples of suitable aqueous and non-aqueous carders, diluents, solvents, or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

The pharmaceutical composition formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

The specific dose and schedule of the compound to obtain the wound healing benefit will, of course, be determined by the particular circumstances of the individual patient including, the size, weight, age and sex of the patient, the nature and stage of the wound or the underlying disease associated with the wound being treated, the aggressiveness of the disease, and the route of administration. For example, a daily dosage of from about 0.01 to about 150 mg/kg/day may be utilized, more preferably from about 0.05 to about 100 mg/kg/day. Particularly preferred are doses from about 1.0 to about 50.0 mg/kg/day, for example, a dose of about 10.0 mg/kg/day. The dose may be given over multiple administrations, for example, two administrations of 5 mg/kg. Higher or lower doses are also contemplated.

Dosage forms for topical administration of pharmaceutical compositions of this invention include powders, sprays, ointments, and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend as upon the activity of the particular pharmaceutical compound or analogue thereof of the present invention, the route of administration, the severity of the condition being treated, and the condition and prior medical history of the patient being treated. However, it is within the skill of the art to start doses of the pharmaceutical compound at levels lower than required to achieve the desired therapeutic effect and to gradually increase the dosage until the desired effect is achieved.

Various delivery systems are known and can be used to administer a composition of the invention, i.e., encapsulation in liposomes, microparticles, microcapsules, etc. The compounds or compositions may be administered together with other biologically active agents. Administration can be systemic or local. In addition, it may be desirable to introduce the pharmaceutical compounds or compositions of the invention into the central nervous system by any suitable route, including intrathecal and intraventricular injection that may be facilitated by an intraventricular catheter, for example, attached to a reservoir, such as an Ommaya reservoir. Pulmonary administration can also be employed, i.e., by use of an inhaler or nebulizer, and formulation with an aerosolizing agent.

Within one embodiment of the invention, the pharmaceutical composition may be prepared for topical administration in saline (combined with any of the preservatives and antimicrobial agents commonly used in ocular preparations), and administered in eye drop form. The solution or suspension may be prepared in its pure form and administered several times daily to a subject prior to or after a radiation event. Alternatively, the pharmaceutical composition, prepared as described above, may also be administered directly to the cornea. Within preferred embodiments, the composition is prepared with a muco-adhesive polymer which binds to cornea. Topical therapy may also be useful pyrophylactically in corneal lesions which are known to have a high probability of inducing an angiogenic response such as chemical burns. In these instances the treatment, likely in combination with steroids, may be instituted immediately to help prevent subsequent complications.

In a sustained-release form injections might only be required 2-3 times per year. A steroid could also be added to the injection solution to reduce inflammation resulting from the injection itself. Within other embodiments, the composition of the invention may be placed in any location to allow its continued release into the aqueous humor.

In a specific embodiment, it may be desirable to administer the pharmaceutical compounds or compositions of the invention locally to the area in need of wound prevention and/or treatment; this may be achieved by, for example, and not by way of limitation, local infusion, topical application, i.e., in conjunction with a wound dressing after surgery, by injection, by means of a catheter, by means of a suppository, or by means of an implant, the implant being of a porous, non-porous, or gelatinous material, including membranes, such as sialastic membranes, or fibers.

In one embodiment, the compound or composition can be delivered in a controlled release system. In one embodiment, a pump may be used (see, Sefton, Biomed. Eng. 14:201 (1987)). In another embodiment, polymeric materials can be used (see, Langer and Peppas, J., Macromol. Sci. Rev. Macromol. Chem. 23:61 (1983); and Levy et al., Science 228:190 (1985)). In yet another embodiment, a controlled release system can be placed in proximity of the target, i.e., the brain, thus requiring only a fraction of the systemic dose. Other controlled release systems are discussed in the review by Langer, Science 249:1527-1533 (1990).

The amount of the compound of the invention which will be effective in the treatment, inhibition and prevention of wounds can be determined by standard clinical techniques. In addition, in vitro assays may optionally be employed to help identify optimal dosage ranges.

In particular, the dosage of the composition of the present invention will depend on clinical factors such as weight and condition of the human or animal and the route of administration of the compound. The precise dose to be employed in the formulation, therefore, should be decided according to the judgment of the practitioner and each patient's circumstances. Effective doses may be extrapolated from dose-response curves derived from in vitro or animal model test systems.

For treating humans or animals, between approximately 0.5 to 500 mg/kilogram is typical broad range for administering the pharmaceutical composition of the invention. The methods of the present invention contemplate single as well as multiple administrations, given either simultaneously or over an extended period of time. It is to be understood that the present invention has application for both human and veterinary use.

The term "effective amount" of the compound as used herein refers to an amount after dilution that is effective to mitigate, reduce or eliminate the wound or the underlying disease associated with the wound in the subject. The compound is administered, for example, in a concentration of about 0.25 micromolar to about 100 micromolar; preferably, from about 1.0 to about 50 micromolar; more preferably from about 2.0 to about 25 micromolar. Particularly preferred concentrations for administration are, for example, about 0.5, 1.0 and 2.5 micromolar and about 5, 10 and 20 micromolar. Higher or lower concentrations may also be used depending upon factors well known in the art.

According to a preferred embodiment, the compound is administered in the form of a pharmaceutical composition comprising ON 01210.Na in combination with at least one stabilizing agent and a pharmaceutically acceptable carrier. ON 01210.Na in such formulations may comprise from 0.1 to 99.99 weight percent. By "pharmaceutically acceptable carrier" is meant any carrier, diluent or excipient, for example a water soluble polymer/cosolvent, which is compatible with the other ingredients of the formulation and is not deleterious to the subject.

Preferred unit dosage formulations are those containing a daily dose or unit, daily sub-dose, as herein above recited, or an appropriate fraction thereof, of the administered ingredient. A single dosage is generally within the range of about 1 ml to about 5 ml of any of the compositions described herein. Individual 3 ml dosages of compositions described herein are contemplated, for example. The dosages may be packaged, for example, in 5 ml vials.

It should be understood that in addition to the ingredients, particularly mentioned above, the formulations of the present invention may include other agents conventional in the art having regard to the type of formulation in question. Where necessary, the composition may also include a solubilizing agent and a local anesthetic such as lignocaine to ease pain at the site of the injection.

The shelf stable formulation may also be filled in a self-injecting device for ease of use by individuals for reducing the size or closure of the wound. Such a device will deliver a pre-determined dose (or doses) of the compound.

For parenteral administration, the compound may be diluted, prior to parenteral administration, with suitable diluents selected from water, saline solution, aqueous dextrose (glucose) and related sugar solutions, propylene glycol or polyethylene glycol. Stabilizing agents, antioxidizing agents, chelating agents, and preservatives, for example, may also be added. Stabilizing agents are preferred and water soluble Vitamin E derivatives are most preferred. Suitable antioxidizing agents include sulfite, ascorbic acid, citric acid and its salts, and sodium EDTA as a chelator, for example. Suitable preservatives include benzalkonium chloride, methyl- or propyl-paraben, and chlorbutanol.

In another embodiment, the compounds of the present invention are formulated with active ingredient, e.g., ON 01210. Na, with a stabilizing agent and a cosolvent buffered at about pH between 7.0 and 8.7. Preferred compositions of the present invention comprise between about 5 mg/ml to about 200 mg/ml of ON 01210. Na in an aqueous solution. In one embodiment, shelf-stable compositions of the present invention, for dilution prior to administration comprise between about 10 mg/ml to about 150 mg/ml of ON 01210. Na. These shelf stable formulations are useful for oral and parenteral administration. In another embodiment, parenteral administration is by the subcutaneous route, Intramuscular route or both. For intravenous administration, if desired, these compositions may be diluted with a suitable parenteral diluent prior to infusion. Compositions of the present invention may, for example, be diluted with about 7 parts diluent (7:1) prior to intravenous administration. However, the dilution factor and the diluent employed depend on the concentration of drug in the formulation. Compositions of the present invention, however, may be diluted with anywhere, for example, within the range of about 2 volumes of suitable parenteral diluent prior to infusion to about 12 volumes of suitable parenteral diluent, prior to intravenous administration.

In one embodiment, the compositions of the present invention for intravenous administration have a pH within the range of about 7.0 to about 9.5 A diluted product pH of about 7.0 to about 8.0 is preferred. The osmolarity of the diluted formulation for parenteral administration should be approximately within the range of about 200 to about 400 mOsm/kg. Preferred osmolarity of the diluted formulation for administration should be approximately within the range of about 270 to about 330 mOsm/kg. A preferred osmolarity of the diluted formulation for administration should be approximately 300 mOsm/kg.

Example compositions of the present invention comprise between about 20 mg/ml to about 150 mg/ml (e.g., about 25 mg/ml, 50 mg/ml, 75 mg/ml, 100 mg/ml, 125 mg/ml, 150 mg/ml) of at least one α,β-unsaturated aryl sulfone (e.g., (E)-4-carboxystyryl-4-chlorobenzylsulfone sodium salt (ON 01210.Na); wherein the composition exhibits a pH within the range of about 7 to about 10. A preferred pH, for example, is between about 8 and about 9, for example. A pH between about 8.3 and about 8.7 is preferred, for example. About 8.5 is an example preferred pH (between about 8.4 and about 8.6). Most preferred buffer is Tris-EDTA, for example, which provides a good physiological buffering capacity at the pH of administration. Exemplary compositions of the present invention described herein exhibit a final concentration of about 0.2M Tris and 0.02M EDTA. However, the Tris concentration may be within a range of about 0.005 M to about 0.5 M (or about 0.005M to about 0.5M "Tris-EDTA", for example) to suit the conditions for administration. Any buffer known in the art to be suitable for injectable formulations may be employed in these compositions of the present invention. Suitable buffering agents, for example, include phosphate buffers, for example, trisodium orthophosphate, disodium hydrogen phosphate, sodium bicarbonate, as well as sodium citrate, potassium citrate, N-methylglucamine, L(+) lysine, glycine and L(+) arginine provide good buffering capacity between about pH 7-9.5, for example.

An example solution composition of the present invention comprises an effective amount of ON 01210. Na in a formulation which comprises between about 10 mg/ml to about 100 mg/ml of the compound (e.g., ON 01210.Na); at least one buffer selected from the group consisting of Tris-EDTA, sodium bicarbonate, sodium citrate, N-methylglucamine, L(+) lysine, glycine, L(+) arginine, and phosphate; a water soluble cosolvent within the range of about 20% w/v to about 60% w/v; a stabilizing agent within the range of about 0.1% w/v to about 10% w/v, and, wherein the composition has a pH within the range of about 8 to about 9. An example composition of the present invention of this type comprises Tris-EDTA buffer within the range of about 0.005M-0.5M; PEG within the range of about 40% w/v to about 60% w/v; wherein the composition has a pH within the range of about 8.3 to about 8.7. A preferred example of this type comprises Tris-EDTA buffer within the range of about 0.1M to about 0.3M (e.g., 0.2M); PEG 400 within the range of about 40% w/v to about 60% w/v (e.g., 50% w/v), and, wherein the composition has a pH within the range of about 8.3 to about 8.7 (e.g., between about 8.4 and about 8.6).

Another example composition of the present invention comprises about 20 mg/ml to about 60 mg/ml of the compound (ON 01210.Na); Tris-EDTA buffer within the range of about 0.15M to about 0.25M; PEG 400 within the range of about 45% w/v to about 55% w/v, wherein the composition has a pH within the range of about 8.4 to about 8.6, and the compound is substantially stable in the composition at from about 25° C. to about 40° C. for at least about 120 days.

Formulations described herein are preferred which have a pH within a range of about 7.5 to about 9.2. High pH, e.g., about 8.5, is preferred. Compositions are preferred that comprise between about 0.5% and about 90% of at least one cosolvent, e.g. at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, and at least about 90%. The term "cosolvent", as used herein, includes but is not limited to water soluble excipients known in the art including water soluble polymers such as polyethylene glycol (PEG) (e.g., PEG 400), polypropylene glycol, polyglycerol, DMA, propylene glycol, glycerol, ethanol, sorbitol, and isopropyl alcohol.

The viscosity of the formulation, for example, may be adjusted using a suitable viscosity modifying agent, for example carboxy methyl cellulose or any of the similar excipients well known in the art. See, e.g., Handbook of Pharmaceutical Excipients, for example. The viscosity modifying agent will be biocompatible and suitable for parenteral administration. The concentration of the suspending agent could vary from 0.1 to 5%. The preferred amount is in the range of about 1%.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drag in liposomes or microemulsions which are compatible with body tissues.

The injectable formulations can be sterilized, for example, by filtration through a bacteria-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Liquid dosage forms for oral administration include pharmaceutically acceptable emulsions, solutions, suspensions, syrups, and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof. Compositions for rectal or vaginal administration are preferably suppositories which can be prepared by mixing the compounds of this invention with suitable non-irritating excipients or carriers such as cocoa butter, polyethylene glycol, or a suppository wax which are solid at room temperature but liquid at body temperature and therefore melt in the rectum or vaginal cavity and release the active compound.

The present invention is illustrated by the Examples that follow, it being understood, however, that the invention is not limited to the specific details of these Examples.

EXAMPLES

Example 1

The Effect of (E)-4-CARBOXYSTYRYL-4-CHLOROBENZYL-SULFONE (ON 1210 Na) on Wound Healing Test substance ON 01210.Na Solution was evaluated for possible effects on wound healing in a mouse model of cutaneous injury. The test substance was administered subcutaneously (SC) in two dosing regimens: the first was 24 hours and 15 minutes before skin punch, and the second was 4 hours and 15 minutes before skin punch. Percent closure of the wound (%) was determined on days 1, 3, 5, 7, 9, 11, 13, 15, 17, 19, 21 and 22, and the half closure time ($CT_{50}$) was then obtained. One-way ANOVA followed by Dunnett's test was used to determine significant difference between vehicle control and treated groups at individual time points. Significant differences are considered at $P<0.05$ level. The results are summarized in the table below:

TABLE 1

THE EFFECT OF (E)-4-CARBOXYSTYRYL-4-CHLOROBENZYL SULFONE ON WOUND HEALING

| Treatment | Route | Dose | | Day 1 | Day 3 | Day 5 | Day 7 | Day 9 | Day 11 | Day 13 |
|---|---|---|---|---|---|---|---|---|---|---|
| Vehicle | SC | 10 mL/kg × 2 | Mean | 0.0 | 6.5 | 16.0 | 32.5 | 55.6 | 69.6 | 80.5 |
| (ON 01210.Na Placebo | | (−4 hr, −15 min) | SEM | 0.0 | 6.5 | 6.8 | 6.5 | 6.0 | 3.1 | 1.9 |
| ON 01210.Na Solution | SC | 500 mg/kg × 2 | Mean | 0.0 | 29.8* | 41.3* | 51.8* | 64.8 | 76.1 | 88.3* |
| | | (−24 hr, −15) | SEM | 0.0 | 3.5 | 1.9 | 1.9 | 3.2 | 2.4 | 2.0 |
| ON 01210.Na Solution | SC | 500 mg/kg × 2 | Mean | 0.0 | 23.0† | 32.1 | 42.7 | 56.8 | 71.7 | 87.5* |
| | | (−4 hr, −15 min) | SEM | 0.0 | 4.9 (2/8 died) | 4.7 | 4.5 | 4.7 | 2.4 | 2.1 |

| Treatment | Route | Dose | | Day 15 | Day 17 | Day 19 | Day 21 | Day 22 | $CT_{50}$ (Days) |
|---|---|---|---|---|---|---|---|---|---|
| Vehicle | SC | 10 mL/kg × 2 | Mean | 91.7 | 97.8 | 100.0 | 100.0 | 100.0 | 9.4 |
| (ON 01210.Na Placebo | | (−4 hr, −15 min) | SEM | 1.1 | 0.9 | 0.0 | 0.0 | 0.0 | 0.6 |

TABLE 1-continued

| | | | | | | | | | |
|---|---|---|---|---|---|---|---|---|---|
| ON 01210.Na Solution | SC | 500 mg/kg × 2 (−24 hr, −15 min) | Mean SEM | 97.0* 1.7 | 100.0* 0.0 | 100.0 0.0 | 100.0 0.0 | 100.0 0.0 | 7.2* 0.3 |
| ON 01210.Na Solution | SC | 500 mg/kg × 2 (−4 hr, −15 min) | Mean SEM | 97.1* 1.1 | 99.4 0.6 | 100.0 0.0 | 100.0 0.0 | 100.0 0.0 | 8.2 0.5 |

The wound closure (%) and wound half-closure time ($CT_{50}$) were determined. One-way ANOVA followed by Dunnett's test was used for comparison between vehicle control and the treated groups.
*P < 0.05, vs. vehicle control.

Subcutaneous administration of ON 01210.Na Solution at 500 mg/kg in the first dosing pattern (24 hours and 15 minutes before skin punch) promoted significant increase in wound closure on days 3, 5, 7, 13, 15 and 17 resulting in a significant reduction in $CT_{50}$ value (7.2±0.3 days vs 9.4±0.6 days in the vehicle control) in the mouse model of cutaneous injury. However, two out of eight animals died on day 2 when the two doses of ON 01210.Na Solution at 500 mg/kg were given at 4 hr and 15 min before skin punch. The interval between the two doses was 3 hr and 45 min vs 23 hr and 45 min in the first dosing pattern. The cause of death is not known. Similarly, the surviving animals exhibited significant increase in wound closure on days 13 and 15; the resulting $CT_{50}$ value (8.2±0.5 days) was slightly lower than vehicle control but the difference was not statistically significant.

ON 01210.Na Solution at 500 mg/kg SC when given in two doses at an interval of 23 hr and 45 min promoted wound healing with significant reduction in $CT_{50}$ value in a mouse model of cutaneous injury Example 2

Test Substance and Dosing Pattern

ON 01210.Na Solution was provided by Onconova Therapeutics Inc in a preformulated form. Test substance was administered subcutaneously (SC) in two dosing patterns, the first was 24 hours and 15 minutes before skin punch, and the second was 4 hours and 15 minutes before skin punch. The dosing time of vehicle (ON 01210.Na Placebo Solution) was given as the second pattern. The dosing volume was 10 mL/kg.
The type of formulation is summarized as follows:

| Test Compound | Vehicle | Solubility[a] | Color | Light Protection[b] | Temperature[c] | Formulation mg/mL |
|---|---|---|---|---|---|---|
| ON 01210.Na Solution | ON 01210.Na Placebo Solution | S | Colorless | N | RT | 50 |

[a] This is based upon visual observation S: soluble; SS: slight soluble I: insoluble (suspension or precipitation)
[b] Y: formula is kept in tube or vial with brown color, or covered with aluminum foil. N: no protection from light
[c] RT: prepared fresh and stored at 20-25° C.. 4° C.: prepared fresh and stored in the refrigerator or kept on ice.

Animals: Male ICR mice weighing 24±2 g were provided by BioLasco Taiwan (under Charles River Laboratories Technology Licensee). Test animals were housed individually in a cage (29×18×13 cm) after skin injury through experiment. All animals were maintained in a controlled temperature (21-23° C.) and humidity (50%-70%) environment with 12 hours light/dark cycles for at least three days in MDS Pharma Services—Taiwan Laboratory prior to use. Free access to standard lab chow for Mice [MF-18 (Oriental Yeast Co., Ltd., Japan)] and reverse osmosis (RO) water was granted. All aspects of this work including housing, experimentation and disposal of animals were performed in general accordance with the Guide for the Care and Use of Laboratory Animals (National Academy Press, Washington, D.C., 1996).

Chemicals: Hexobarbital (Sigma, USA), Phosphate buffered saline (Sigma, USA) and Sodium Chloride (Wako, Japan).

Equipment: Animal Cage (Allentown, USA), Image—ProPlus (Media Cybernetics, Version 4.5.0.29), Pipetman (Gilson, France) and Sharp Punch, ID 12 mm (Sinter, R. O. C.).

Method: Wound Healing in Skin

Groups of 8 ICR male mice weighing 24±2 g were used. During the study, the tested animals were housed in individual cages. Under hexobarbital (90 mg/kg, IP) anesthesia, the shoulder and back region of each animal was shaved. A sharp punch (ID 12 mm) was applied to remove the skin including panniculus carnosus and adherent tissues. Test substance was administered subcutaneously in two dosing patterns, the first was 24 hours and 15 minutes before skin punch, and the second was 4 hours and 15 minutes before skin punch the dosing time of vehicle (ON 01210.Na Placebo Solution) was given as the second dosing pattern. The wound area, traced onto clear plastic sheets, was measured by use of an Image—ProPlus (Media Cybernetics, Version 4.5.0.29) on days 1, 3, 5, 7, 9, 11, 13, 15, 17, 19, 21 and 22. The percent closure of the wound (%) was calculated, and wound half-closure time ($CT_{50}$) was analyzed by linear regression using Graph-Prism (Graph Software USA). One-way ANOVA followed by Dunnett's test was applied for comparison between the treated and vehicle groups at each measurement time point. Differences are considered statistically significant at P<0.05.

TABLE 2

Wound Healing In the Skin of Mouse (Days 1-11)

| Treatment | Route | Dose | N | The Closure of Wound (%), Individual Value | | | | | |
|---|---|---|---|---|---|---|---|---|---|
| | | | | Day 1 | Day 3 | Day 5 | Day 7 | Day 9 | Day 11 |
| Vehicle (ON 01210.Na Placebo Solution) | SC | 10 mL/kg kg × 2 (−4 hr, −15 min) | 1 | 0.0 | 18.3 | 26.6 | 40.2 | 53.3 | 64.8 |
| | | | 2 | 0.0 | 0.0 | 13.9 | 39.9 | 63.2 | 77.1 |
| | | | 3 | 0.0 | 27.0 | 39.7 | 61.3 | 72.6 | 74.2 |

TABLE 2-continued

Wound Healing In the Skin of Mouse (Days 1-11)

| Treatment | Route | Dose | N | Day 1 | Day 3 | Day 5 | Day 7 | Day 9 | Day 11 |
|---|---|---|---|---|---|---|---|---|---|
| | | | 4 | 0.0 | 21.5 | 31.5 | 45.3 | 75.2 | 81.4 |
| | | | 5 | 0.0 | −6.9 | −2.3 | 13.7 | 39.5 | 62.5 |
| | | | 6 | 0.0 | −24.3 | −4.9 | 14.5 | 39.1 | 56.0 |
| | | | 7 | 0.0 | 21.9 | 32.9 | 35.8 | 69.5 | 76.2 |
| | | | 8 | 0.0 | −5.9 | −9.2 | 9.2 | 32.7 | 64.5 |
| | | | Mean | 0.0 | 6.5 | 16.0 | 32.5 | 55.6 | 69.6 |
| | | | SEM | 0.0 | 6.5 | 6.8 | 6.5 | 6.0 | 3.1 |
| PT# 1123812 (OH-40) (ON 01210.Na Solution) | SC | 500 mg/kg × 2 (−24 hr, −15 min) | 1 | 0.0 | 36.8 | 51.5 | 49.7 | 74.1 | 79.5 |
| | | | 2 | 0.0 | 15.2 | 35.7 | 47.0 | 60.1 | 81.7 |
| | | | 3 | 0.0 | 28.2 | 39.1 | 45.6 | 54.4 | 70.4 |
| | | | 4 | 0.0 | 23.1 | 45.1 | 56.9 | 63.6 | 76.3 |
| | | | 5 | 0.0 | 21.6 | 37.7 | 46.8 | 54.1 | 64.4 |
| | | | 6 | 0.0 | 42.8 | 35.6 | 60.4 | 79.4 | 84.4 |
| | | | 7 | 0.0 | 29.4 | 40.9 | 52.0 | 64.0 | 71.4 |
| | | | 8 | 0.0 | 41.1 | 44.4 | 55.8 | 69.1 | 80.8 |
| | | | Mean | 0.0 | 29.8 | 41.3 | 51.8 | 64.8 | 76.1 |
| | | | SEM | 0.0 | 3.5 | 1.9 | 1.9 | 3.2 | 2.4 |
| | | | P | | * | * | * | | |
| PT# 1123812 (OH-40) (ON 01210.Na Solution) | SC | 500 mg/kg × 2 (−4 hr, −15 min) | 1 | 0.0 | 27.9 | 40.2 | 48.0 | 59.0 | 65.3 |
| | | | 2 | 0.0 | 13.0 | 23.3 | 32.9 | 49.2 | 68.7 |
| | | | 3 | 0.0 | 31.4 | 37.2 | 41.9 | 60.3 | 73.5 |
| | | | 4 | 0.0 | 13.4 | 24.9 | 36.2 | 52.9 | 77.1 |
| | | | 5 | 0.0 | 40.5 | 48.5 | 62.4 | 76.3 | 79.6 |
| | | | 6 | 0.0 | 11.7 | 18.4 | 34.6 | 43.0 | 66.1 |
| | | | 7 | 0.0 | died | died | Died | died | Died |
| | | | 8 | 0.0 | died | died | Died | died | Died |
| | | | Mean | 0.0 | 23.0 | 32.1 | 42.7 | 56.8 | 71.7 |
| | | | SEM | 0.0 | 4.9 | 4.7 | 4.5 | 4.7 | 2.4 |
| | | | P | | | | | | |

TABLE 3

Wound Healing In the Skin of Mouse (Days 13-22)

| Treatment | Route | Dose | N | Day 13 | Day 15 | Day 17 | Day 19 | Day 21 | Day 22 | $CT_{50}$ (Days) |
|---|---|---|---|---|---|---|---|---|---|---|
| Vehicle (ON 01210.Na Placebo Solution) | SC | 10 mL/kg kg × 2 (−4 hr, −15 min) | 1 | 74.7 | 87.9 | 95.3 | 100.0 | 100.0 | 100.0 | 9.2 |
| | | | 2 | 84.9 | 94.0 | 100.0 | 100.0 | 100.0 | 100.0 | 9.2 |
| | | | 3 | 87.6 | 94.1 | 100.0 | 100.0 | 100.0 | 100.0 | 7.1 |
| | | | 4 | 84.2 | 89.8 | 94.1 | 100.0 | 100.0 | 100.0 | 7.9 |
| | | | 5 | 75.3 | 86.4 | 95.8 | 100.0 | 100.0 | 100.0 | 11.0 |
| | | | 6 | 73.9 | 94.6 | 100.0 | 100.0 | 100.0 | 100.0 | 11.3 |
| | | | 7 | 82.9 | 92.6 | 96.9 | 100.0 | 100.0 | 100.0 | 8.3 |
| | | | 8 | 80.3 | 93.9 | 100.0 | 100.0 | 100.0 | 100.0 | 11.0 |
| | | | Mean | 80.5 | 91.7 | 97.8 | 100.0 | 100.0 | 100.0 | 9.4 |
| | | | SEM | 1.9 | 1.1 | 0.9 | 0.0 | 0.0 | 0.0 | 0.6 |
| PT# 1123812 (OH-40) (ON 01210.Na Solution) | SC | 500 mg/kg kg × 2 (−24 hr, −15 min) | 1 | 84.4 | 89.8 | 100.0 | 100.0 | 100.0 | 100 | 6.6 |
| | | | 2 | 90.6 | 100.0 | 100.0 | 100.0 | 100.0 | 100.0 | 8.0 |
| | | | 3 | 83.7 | 100.0 | 100.0 | 100.0 | 100.0 | 100.0 | 8.0 |
| | | | 4 | 89.6 | 100.0 | 100.0 | 100.0 | 100.0 | 100.0 | 7.2 |
| | | | 5 | 85.8 | 97.6 | 100.0 | 100.0 | 100.0 | 100.0 | 8.3 |
| | | | 6 | 95.8 | 100.0 | 100.0 | 100.0 | 100.0 | 100.0 | 6.0 |
| | | | 7 | 80.7 | 88.8 | 100.0 | 100.0 | 100.0 | 100.0 | 7.6 |
| | | | 8 | 95.6 | 100.0 | 100.0 | 100.0 | 100.0 | 100 | 6.2 |
| | | | Mean | 88.3 | 97.0 | 100.0 | 100.0 | 100.0 | 100.0 | 7.2 |
| | | | SEM | 2.0 | 1.7 | 0.0 | 0.0 | 0.0 | 0.0 | 0.3 |
| | | | P | * | * | * | | | | * |
| PT# 1123812 (OH-40) (ON 01210.Na Solution) | SC | 500 mg/kg kg × 2 (−4 hr, −15 min) | 1 | 84.2 | 93.4 | 96.7 | 100.0 | 100.0 | 100.0 | 8.0 |
| | | | 2 | 90.4 | 94.6 | 100.0 | 100.0 | 100.0 | 100.0 | 9.2 |
| | | | 3 | 90.3 | 97.2 | 100.0 | 100.0 | 100.0 | 100.0 | 7.7 |
| | | | 4 | 78.8 | 100.0 | 100.0 | 100.0 | 100.0 | 100.0 | 8.9 |
| | | | 5 | 93.1 | 97.6 | 100.0 | 100.0 | 100.0 | 100.0 | 5.8 |
| | | | 6 | 88.0 | 100.0 | 100.0 | 100.0 | 100.0 | 100.0 | 9.4 |
| | | | 7 | died | died | Died | Died | died | died | — |
| | | | 8 | died | died | Died | Died | died | died | — |
| | | | Mean | 87.5 | 97.1 | 99.4 | 100.0 | 100.0 | 100.0 | 8.2 |
| | | | SEM | 2.1 | 1.1 | 0.6 | 0.0 | 0.0 | 0.0 | 0.5 |
| | | | P | * | * | | | | | |

Test substance was administered subcutaneously (SC) in two dosing patterns, the first was 24 hours and 15 minutes before skin punch, and the second was 4 hours and 15 minutes before skin punch; the dosing time of vehicle (ON 01210.Na Placebo Solution) was given as the second pattern. The wound closure (%) and wound half-closure time ($CT_{50}$) were determined. One-way ANOVA followed by Dunnett's test was applied for comparison between the treated and vehicle groups. *$P<0.05$, vs. vehicle control.

EQUIVALENTS

The above examples have been depicted solely for the purpose of exemplification and are not intended to restrict the scope or embodiments of the invention. Other embodiments not specifically described should be apparent to those of ordinary skill in the art. Such other embodiments are considered to fall, nevertheless, within the scope and spirit of the present invention. Thus, the invention is properly limited solely by the claims that follow.

What is claimed is:

1. A method for promoting rapid healing and/or regeneration of damaged tissue resulting from a wound comprising administering to a subject in need thereof a therapeutically effective amount of a pharmaceutical composition comprising a compound which is (E)-4-carboxystyryl-4-chlorobenzylsulfone, or a pharmaceutically acceptable salt thereof, wherein said pharmaceutical composition promotes rapid healing and/or regeneration of damaged tissues while retaining original composition of the tissue and minimizing complications and scarring.

2. The method of claim 1, wherein the administration to the subject is performed prior to the incident of the wound.

3. The method of claim 2, wherein the administration to the subject is performed about 4 hours prior to the incident of the wound.

4. The method of claim 2, wherein the administration to the subject is performed about 24 hours prior to the incident of the wound.

5. The method of claim 1, wherein the compound is ON 01210.Na.

6. The method of claim 5, wherein ON 01210.Na is formulated in an aqueous solution composition comprising between about 20 mg/ml to about 100 mg/ml of ON 01210.Na, at least one cosolvent comprising polyethylene glycol (PEG), polypropylene glycol, polyglycerol, DMA, propylene glycol, glycerol, ethanol, sorbitol, and isopropyl alcohol, or a combination thereof, in an amount between about 25% and about 90% w/v wherein the composition has a pH within the range of about 7.0 to about 9.5.

7. The method of claim 1, wherein the composition is administered by parenteral route.

8. The method of claim 1, wherein the composition is administered by topical route.

9. The method of claim 1, wherein the composition is administered by oral route.

* * * * *

UNITED STATES PATENT AND TRADEMARK OFFICE
CERTIFICATE OF CORRECTION

PATENT NO.       : 9,044,427 B2  
APPLICATION NO.  : 13/636305  
DATED            : June 2, 2015  
INVENTOR(S)      : Kumar et al.

Page 1 of 1

It is certified that error appears in the above-identified patent and that said Letters Patent is hereby corrected as shown below:

Title Page, Item (75) Inventor is corrected to read:
-- Ramesh Kumar, Pennington (NJ);
   Manoj Manior, Fremont (CA); --.

Signed and Sealed this
Twenty-fifth Day of August, 2015

Michelle K. Lee
*Director of the United States Patent and Trademark Office*